(12) United States Patent
Dranoff et al.

(10) Patent No.: US 10,865,233 B2
(45) Date of Patent: Dec. 15, 2020

(54) NKG2D-FC FOR IMMUNOTHERAPY

(75) Inventors: Glenn Dranoff, Lexington, MA (US); Matthew Vanneman, Boston, MA (US); Gordon Freeman, Brookline, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 534 days.

(21) Appl. No.: 13/140,469

(22) PCT Filed: Dec. 18, 2009

(86) PCT No.: PCT/US2009/006627
§ 371 (c)(1),
(2), (4) Date: Sep. 8, 2011

(87) PCT Pub. No.: WO2010/080124
PCT Pub. Date: Jul. 15, 2010

(65) Prior Publication Data
US 2011/0311535 A1 Dec. 22, 2011

Related U.S. Application Data

(60) Provisional application No. 61/138,715, filed on Dec. 18, 2008.

(51) Int. Cl.
C07K 14/705 (2006.01)
A61K 38/17 (2006.01)
A61K 45/06 (2006.01)

(52) U.S. Cl.
CPC ...... *C07K 14/70596* (2013.01); *A61K 38/177* (2013.01); *A61K 45/06* (2013.01); *C07K 14/7056* (2013.01); *C07K 2319/30* (2013.01)

(58) Field of Classification Search
CPC ...... A61K 6/00; A61K 38/00; A61K 2008/00; A61K 2039/00; A61K 2039/505; C07K 1/00; C07K 14/00; C07K 14/435; C07K 14/705; C07K 14/70503; C07K 14/70539; C12N 1/00
See application file for complete search history.

(56) References Cited

U.S. PATENT DOCUMENTS

| | | | |
|---|---|---|---|
| 5,739,281 A * | 4/1998 | Thoøgersen et al. | 530/350 |
| 6,992,174 B2 | 1/2006 | Gillies et al. | |
| 7,250,493 B2 | 7/2007 | Sun et al. | |
| 2002/0187151 A1 * | 12/2002 | Raulet et al. | 424/155.1 |
| 2006/0252096 A1 | 11/2006 | Zha et al. | |
| 2008/0299137 A1 * | 12/2008 | Svendsen et al. | 424/178.1 |
| 2009/0281035 A1 | 11/2009 | Spee et al. | |
| 2010/0068137 A1 | 3/2010 | Chang et al. | |
| 2011/0177070 A1 | 7/2011 | Lofquist et al. | |

FOREIGN PATENT DOCUMENTS

| | | |
|---|---|---|
| WO | WO 2005/097160 A2 | 10/2005 |
| WO | WO 2006/107124 A | 10/2006 |
| WO | WO 2007/002905 A1 | 1/2007 |
| WO | WO 2008/036981 A1 | 3/2008 |
| WO | WO 2008/067305 A2 | 6/2008 |
| WO | WO 2015/036606 A1 | 3/2015 |

OTHER PUBLICATIONS

Bioscience Technology (Apr. 1, 2003).*
[No Author Listed] Recombinant Human NKG2D/Fc Chimera. Bioscience Technology. Apr. 8, 2003. Retrieved from <http://www.biosciencetechnology.com/articles/2003/04/recombinant-human-nkg2d-fc-chimera> on Aug. 24, 2015.
International Search Report and Written Opinion for PCT/US2016/061479 dated Feb. 1, 2017.
Extended European Search Report for EP09837720 dated Sep. 14, 2012.
International Search Report and Written Opinion for PCT/US2009/006627 dated Sep. 27, 2010.
International Preliminary Report on Patentability for PCT/US2009/006627 dated Jun. 30, 2011.
Cartron et al., Therapeutic activity of humanized anti-CD20 monoclonal antibody and polymorphism in IgG Fc receptor FcgammaRIIIa gene. Blood. Feb. 1, 2002;99(3):754-8.
Chen et al., Fusion protein linkers: property, design and functionality. Adv Drug Deliv Rev. Oct. 2013;65(10):1357-69. doi:10.1016/j.addr.2012.09.039. Epub Sep. 29, 2012.
Genbank Submission; NIH/NCBI Accession No. AAX37025.1. Hines et al., Mar. 16, 2005.
Genbank Submission; NIH/NCBI, Accession No. AAP69528.1. Rieder et al., Aug. 19, 2003.
Nimmerjahn et al., Fcgamma receptors: old friends and new family members. Immunity. Jan. 2006;24(1):19-28.
Rowley et al., Expression of IL-15RA or an IL-15/IL-15RA fusion on CD8+ T cells modifies adoptively transferred T-cell function in cis. Eur J Immunol. Feb. 2009;39(2):491-506. doi:.10.1002/eji.200838594.
Zhang et al., Immune surveillance and therapy of lymphomas driven by Epstein-Barr virus protein LMP1 in a mouse model. Cell. Feb. 17, 2012;148(4):739-51. doi:10.1016/j.cell.2011.12.031.
Ashkenazi et al., Immunoadhesins as research tools and therapeutic agents. Curr Opin Immunol. Apr. 1997;9(2):195-200.
Bell, Natural killer cells: Dual role for NKG2D. The Signaling Gateway. Jul. 15, 2008. Last accessed at http://www.signaling-gateway.org/update/updates/200301/nri988.html on Nov. 28, 2011. p. 1-2.

(Continued)

*Primary Examiner* — Alana Harris Dent
(74) *Attorney, Agent, or Firm* — Wolf, Greenfield & Sacks, P.C.

(57) ABSTRACT

Methods for cancer immunotherapy are provided. The methods involve the use of a chimeric molecule (e.g., fusion protein) comprising an NKG2D portion and an Fc portion, which binds one or more NKG2D ligands. The methods disclosed herein are useful for the treatment of cancer that is associated with abnormal expression of one or more NKG2D ligands.

14 Claims, 9 Drawing Sheets

Specification includes a Sequence Listing.

(56) References Cited

OTHER PUBLICATIONS

Caillat-Zucman, How NKG2D ligands trigger autoimmunity? Hum Immunol. Mar. 2006;67(3):204-7. Epub Mar. 31, 2006.
Carrasco et al., The differentiation and stress response factor XBP-1 drives multiple myeloma pathogenesis. Cancer Cell. Apr. 2007;11(4):349-60.
Dougan et al., Inciting inflammation: the RAGE about tumor promotion. J Exp Med. Feb. 18, 2008;205(2):267-70. Epub Feb. 11, 2008.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.
Fonseca et al., Capitalizing on the immunogenicity of dying tumor cells. Clin Cancer Res. Mar. 15, 2008;14(6):1603-8.
Garrity et al., The activating NKG2D receptor assembles in the membrane with two signaling dimers into a hexameric structure. Proc Natl Acad Sci U S A. May 24, 2005;102(21):7641-6. Epub May 13, 2005.
Gasser et al., The DNA damage pathway regulates innate immune system ligands of the NKG2D receptor. Nature. Aug. 25, 2005;436(7054):1186-90. Epub Jul. 3, 2005.
Genbank Submission; NIH/NCBI, Accession No. NP_031386. Liu et al., Oct. 21, 2012. 3 pages.
González et al., Immunobiology of human NKG2D and its ligands. Curr Top Microbiol Immunol. 2006;298:121-38.
Guerra et al., NKG2D-deficient mice are defective in tumor surveillance in models of spontaneous malignancy. Immunity. Apr. 2008;28(4):571-80. Erratum in: Immunity. May 2008;28(5):723.
Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10. Epub Feb. 19, 2008.
Jinushi et al., Therapy-induced antibodies to MHC class I chain-related protein a antagonize immune suppression and stimulate antitumor cytotoxicity. Proc Natl Acad Sci U S A. Jun. 13, 2006;103(24):9190-5. Epub Jun. 5, 2006.
Jinushi et al., Immunosurveillance:Innate and Adaptive Anti-tumor Immunity. In Cancer Immunotherapy: Immune Suppression and Tumor Growth. Eds. CG Prendergrast and EM Jaffee. Cancer Immunother. 2007; pp. 29-41.
Jinushi et al., MFG-E8-mediated uptake of apoptotic cells by APCs links the pro- and antiinflammatory activities of GM-CSF. J Clin Invest. Jul. 2007;117(7):1902-13.
Jinushi et al., Enhancing the clinical activity of granulocyte-macrophage colony-stimulating factor-secreting tumor cell vaccines. Immunol Rev. Apr. 2008;222:287-98.
Jinushi et al., MHC class I chain-related protein a antibodies and shedding are associated with the progression of multiple myeloma. Proc Natl Acad Sci U S A. Jan. 29, 2008;105(4):1285-90. Epub Jan. 17, 2008.
Kaneko et al., Anti-inflammatory activity of immunoglobulin G resulting from Fc sialylation. Science. Aug. 4, 2006;313(5787):670-3.
Kobayashi et al., TIM-1 and TIM-4 glycoproteins bind phosphatidylserine and mediate uptake of apoptotic cells. Immunity. Dec. 2007;27(6):927-40.
Kotturi et al., Tumor cells expressing a fusion protein of MULT1 and Fas are rejected in vivo by apoptosis and NK cell activation. Gene Ther. Oct. 2008;15(19):1302-10.
Lanier, NK cell recognition. Annu Rev Immunol. Apr. 2005;23:225-74.
Lengyel et al., Mutations designed to destabilize the receptor-bound conformation increase MICA-NKG2D association rate and affinity. J Biol Chem. Oct. 19, 2007;282(42):30658-66. Epub Aug. 8, 2007.
Lin et al., Modeling genomic diversity and tumor dependency in malignant melanoma. Cancer Res. Feb. 1, 2008;68(3):664-73.
Liu et al., Engineering therapeutic monoclonal antibodies. Immunol Rev. Apr. 2008;222:9-27.
Nimmerjahn et al., Antibodies, Fc receptors and cancer. Curr Opin Immunol. Apr. 2007;19(2):239-45. Epub Feb. 8, 2007.
Ogasawara et al., Function of NKG2D in natural killer cell-mediated rejection of mouse bone marrow grafts. Nat Immunol. Sep. 2005;6(9):938-45. Epub Aug. 7, 2005.
Poggi et al., NKG2D and natural cytotoxicity receptors are involved in natural killer cell interaction with self-antigen presenting cells and stromal cells. Ann N Y Acad Sci. Aug. 2007;1109:47-57.
Polzin et al., Involvement of ral GTP-ases in the regulation of synaptic exocytosis. Abstract—30th Annual Society for Neuroscience Meeting. Nov. 2000. 1 page.
Strong et al., NKG2D and Related Immunoreceptors. Adv Protein Chem. Nov. 5, 2004;68:281-312.
Strong, Asymmetric ligand recognition by the activating natural killer cell receptor NKG2D, a symmetric homodimer. Mol Immunol. May;38(14):1029-37, 2001.
Unni et al., Intrinsic sensor of oncogenic transformation induces a signal for innate immunosurveillance. Proc Natl Acad Sci U S A. Feb. 5, 2008;105(5):1686-91. Epub Jan. 25, 2008.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Zhang et al., Alteration in the IL-2 signal peptide affects secretion of proteins in vitro and in vivo. J Gene Med. Mar. 2005;7(3):354-65.
Zhang et al., Generation of antitumor responses by genetic modification of primary human T cells with a chimeric NKG2D receptor. Cancer Res. Jun. 1, 2006;66(11):5927-33.
Zhou et al., NKG2D recognition mediates Toll-like receptor 3 signaling-induced breakdown of epithelial homeostasis in the small intestines of mice. Proc Natl Acad Sci U S A. May 1, 2007;104(18):7512-5. Epub Apr. 26, 2007.

\* cited by examiner

Figure 1: NKG2D/Fc fusion protein. The N-terminal region consists of the hinge (allowing for di-sulfide bonding to form a dimer) and $C_H2$ and $C_H3$ domains of a mouse IgG2a molecule, followed by a four amino acid linker (IEGR), and then the extracellular domain of the mouse NKG2D molecule at the C-terminal end.

Figure 2: The NKG2D/Fc gene. An N-terminal modified IL2 signal sequence allows for optimal expression and secretion of NKG2D/Fc construct. Following the signal sequence is the mIgG2a Fc region, the IEGR linker and the extracellular portion of the NKG2D molecule at the C-terminus.

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 1

Ile Glu Gly Arg
1

<210> SEQ ID NO 2
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 2

Gly Gly Pro Leu Gly Leu Trp Ala Gly Gly
1               5                   10
```

NKG2D-FC FOR IMMUNOTHERAPY

REFERENCE TO RELATED APPLICATIONS

This application is a national stage filing under 35 U.S.C. § 371 of international application PCT/US2009/006627, filed Dec. 18, 2009, which was published under PCT Article 21(2) in English, and claims the benefit under 35 U.S.C. § 119(e) to U.S. Provisional Application Ser. No. 61/138,715, filed on Dec. 18, 2008, the disclosure of each referenced application is incorporated by reference in its entirety, including all drawings and all parts of the specification.

GOVERNMENT SUPPORT

This invention was made with government support under grant numbers CA078378 and CA111506 awarded by The National Institutes of Health. The government has certain rights in the invention.

FIELD OF THE DISCLOSURE

The invention relates to therapeutic uses of a chimeric construct that binds to NKG2D ligands. More specifically, the invention provides methods for treating cancer using the NKG2D ligand-binding chimera.

BACKGROUND OF THE DISCLOSURE

NKG2D is a type II transmembrane glycoprotein having an extracellular lectin-like domain. This domain lacks the recognizable calcium-binding sites found in true C-type lectins and binds protein rather than carbohydrate ligands. NKG2D is an activating receptor that is expressed in a variety of immune cells. Human NKG2D is expressed on CD8+αβ T cells, γδ T cells, NK cells and NKT cells. In mouse systems NKG2D also occurs on macrophages. Human ligands for NKG2D include MHC class I chain-related molecules (MICA and MICB), UL16-binding proteins (ULBP1, ULBP2, ULBP3 and ULBP4) and RAET-1G; and mouse ligands for NKG2D include minor histocompatibility antigen 60 (H60) and retinoic acid early inducible transcript (RAE-1). Expression of NKG2D ligands also occurs in intestinal epithelial cells, tumor cells and under conditions of stress or infection.

NKG2D exists as a disulfide-linked homodimer that delivers an activating signal upon ligand binding. Signaling requires association with an adapter protein. Alternative splicing of the NKG2D mRNA results in isoforms with different cytoplasmic domains that can associate either with DAP12 to deliver a true activating signal or with DAP10 resulting in a costimulatory signal. NKG2D has been implicated in immune surveillance and the immune response against viral infection. In addition, elevated levels of NKG2D ligands have been detected in proliferating cells and many types of cancer. Based on this observation, it has been suggested that expression levels of NKG2D ligands, MICA in particular, may provide useful information for the detection and/or diagnosis of cancer.

To that end, earlier studies targeting the NKG2D pathway with respect to potential cancer immunotherapy focused on monoclonal antibodies made against MICA. Detailed description of such work is provided, for example, in International Application, PCT/US2007/079342, entitled "Methods for treating MICA-related disorders," published as WO 2008/036981 A1. Briefly, it was observed that induction of high-titer antibodies against MICA in cancer patients elicited an anti-tumor response. The inventors of the above-referenced international application also disclose that double-stranded DNA breaks triggered high-level expression of MICA in a broad range of human cancers. In addition, it was observed that MICA was also shed by tumor cells, i.e., released from the cell surface into the surrounding medium, and sera from cancer patients typically contained elevated levels of the soluble (shed) MICA.

SUMMARY OF THE DISCLOSURE

In the present disclosure, novel methods for cancer therapy are provided. In particular, the methods described herein involve stimulating an anti-tumor immune response by modulating the NKD2D receptor signaling function. The present invention is based at least in part on the unexpected finding that a chimeric molecule comprising an NKG2D fragment and an Fc fragment, which is capable of binding one or more NKG2D ligands, can induce tumor cell destruction.

Accordingly, the invention relates to methods for treating cancer using an NKG2D-Fc chimera, which is a chimeric or fusion molecule that comprises a NKG2D receptor portion and an Fc portion that binds to an activating Fc receptor and/or fixes complement. As described in more detail herein, the NKG2D-Fc chimera is capable of binding one or more native NKG2D ligands that are expressed in cancer cells. The method comprises administering to a subject having a cancer, where the cancer is characterized by expression of at least one NKG2D ligand, a composition comprising a NKG2D-Fc chimera and a pharmaceutically acceptable carrier, in an amount effective to treat the cancer, wherein the NKG2D-Fc chimera binds a NKG2D ligand.

In some embodiments, the NKG2D-Fc chimera comprises a linking molecule which is not a contiguous portion of either NKG2D or Fc and which covalently joins an amino acid of NKG2D to an amino acid of Fc. For example, in some cases, the linking molecule is a peptide linker. In certain embodiments, the peptide linker may be an IEGR (SEQ ID NO: 1) linker.

In some embodiments, the invention provides that the NKG2D-Fc chimera comprises an NKG2D extracellular domain.

In any of the embodiments provided herein, the NKG2D-Fc chimera may be a recombinant fusion protein.

In some embodiments, the NKG2D ligand-expressing cancer is melanoma, lung cancer, plasma cell cancer, leukemia, lymphoma, ovarian cancer, colon cancer, pancreatic cancer or prostate cancer. In some circumstances, one or more of these cancers may be present in a subject.

According to the invention, any of the methods described herein may further comprise treating the subject with an additional cancer therapy that is not the NKG2D-Fc chimera. For example, the methods provided herein may be used in conjunction with one or more of additional cancer therapies, such as, without limitation, an immunotherapy, a radiation therapy and a chemotherapy.

In preferred embodiments, the additional cancer therapy is a chemotherapy that damages DNA.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

DETAILED DESCRIPTION OF THE DISCLOSURE

Figure 1:
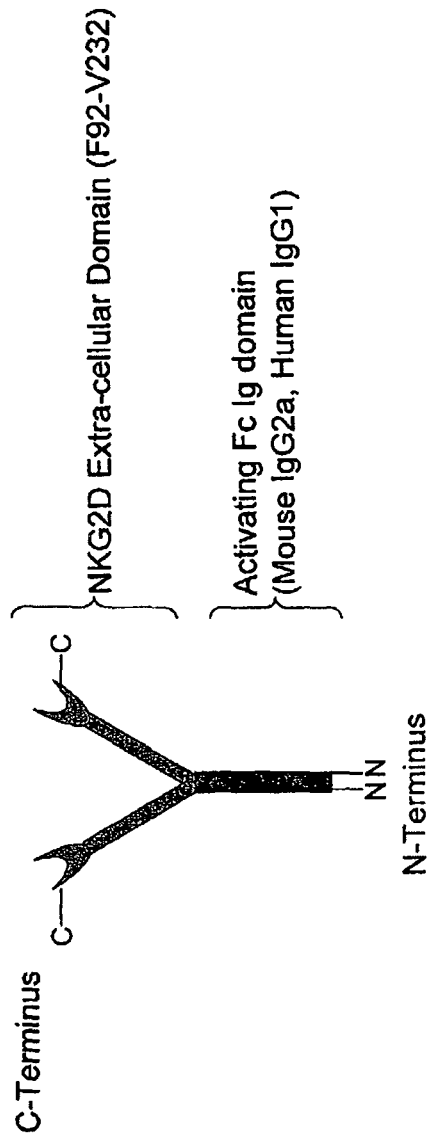
FIG. 1 illustrates the structure of an exemplary dimerized NKG2D/Fc fusion protein. In this embodiment, the N-terminal region consists of the hinge (allowing for disulfide bonding to form a dimer) and $C_H2$ and $C_H3$ domains of a mouse IgG2a molecule, followed by a four amino acid linker (IEGR; SEQ ID NO: 1), and then the extracellular domain of the mouse NKG2D molecule at the C-terminal end.

Disclosed herein are novel methods for cancer immunotherapy. The methods described herein are based on the surprising finding that a chimeric molecule that is capable of binding NKG2D ligands can exert therapeutic effects in cancer models. This construct is believed to be broadly useful for immunotherapy for a wide variety of cancers, where the expression of one or more NKG2D ligands is elevated in a subject.

Unlike the approaches taken previously, which focused on the use of antibodies that specifically recognize a ligand of NKG2D, MICA in particular, the methods provided herein are drawn to a broader class of targets in cancer, namely, NKG2D ligands. Thus, the methods for cancer immunotherapy described herein directly target NKG2D receptor signaling, which is mediated by a number of cellular ligands, including, but not limited to MICA. The invention disclosed herein involves a chimeric molecule, NKG2D-Fc, having the ability to bind one or more ligands for the NKG2D receptor. By virtue of this binding function, NKG2D-Fc can induce immune responses that target tumor cells, thereby eliciting anti-tumor activities.

A human NKG2D-Fc construct is commercially available (R&D Systems) and has been used for laboratory research purposes, e.g., for detecting cancer cells that are associated with elevated MICA expression.

As described below, surprisingly, it has been discovered that a chimeric construct, which is not an antibody, that is capable of binding NKG2D ligands can mediate immunotherapeutic effects in a wide variety of tumor cell types.

As described in more detail below, a fusion protein was constructed that comprises the ligand-binding domain of NKG2D, coupled to the Fc region of an IgG. Data presented herein demonstrate that murine NKG2D fused to the Fc region of murine IgG2a binds both recombinant soluble NKG2D ligands in an ELISA and native ligands expressed on the tumor cell surface. The work described herein demonstrates that the NKG2D-Fc chimeric construct mediates potent and specific complement-dependent lysis, antibody-dependent cellular cytotoxicity, and efficient opsonization of NKG2D ligand-expressing tumor cells.

Accordingly, the invention includes methods for cancer therapy in human, using the human equivalent of the murine NKG2D-Fc, e.g., the ligand-binding domain of human NKG2D coupled to the Fc region of human IgG1. Unlike an immunotherapy that employs a monoclonal antibody against an NKG2D ligand, such as MICA, the methods provided herein are believed to have broad effects against cancer, on the basis that NKG2D binds to multiple ligands.

The NKG2D-Fc chimera can target any or all NKG2D ligands that are expressed on human tumor cells, and thus is capable of mediating tumor cell destruction through complement lysis and ADCC. The NKG2D-Fc chimera is also capable of opsonizing any tumor cells that express at least one NKG2D ligand. The NKG2D-Fc chimera can promote efficient cross-presentation (e.g., priming) by dendritic cells, leading to the induction of potent T cell responses against the tumor. Moreover, this chimera is capable of binding and sequestering any "shed" (e.g., soluble or released) NKG2D ligand(s) produced by tumor cells, thereby alleviating immune suppression due to down-regulation of NKG2D expression in response to tumor-derived soluble ligands.

Finally, the cDNA sequences encoding an NKG2D-Fc fusion polypeptide may be introduced into tumor cells, which can function additionally as a vaccine adjuvant.

A human NKG2D-Fc is commercially available from, for example, R&D Systems, and to date has been used in flow cytometry to detect NKG2D ligands for laboratory studies. It has been unexpectedly discovered, however, that this chimera may exert superior immunotherapeutic effects, as compared to monoclonal antibodies against NKG2D ligands, such as MICA, which are associated with certain types of cancer. As described in detail below, NKG2D-Fc may be useful as a therapeutic reagent, particularly for cancer immunotherapy.

Throughout the disclosure, the term "polypeptide" shall refer to a compound of two or more subunit amino acids (e.g., residues), amino acid analogs, or other peptidomimetics, regardless of post-translational modification, e.g., phosphorylation and glycosylation. The subunits may be linked by peptide bonds or other bonds, such as, for example, ester and ether bonds. As used herein, the term "amino acid" refers to natural and/or unnatural or synthetic amino acids, including D/L optical isomers. Full-length proteins, analogs, mutants, and fragments thereof, are encompassed by this definition.

NKG2D-Fc

The art is familiar with chimeric proteins that combine the Fc regions of IgG with one or more domains of another protein, such as various cytokines and soluble receptors. See, for example, Capon et al., Nature, 337:525-531, 1989; Chamow et al., Trends Biotechnol., 14:52-60, 1996); U.S. Pat. Nos. 5,116,964 and 5,541,087. The prototype fusion protein is a homodimeric protein linked through cysteine residues in the hinge region of IgG Fc, resulting in a molecule similar to an IgG molecule without the $C_H1$ domains and light chains. Due to the structural homology, such Fc fusion proteins exhibit in vivo pharmacokinetic profile comparable to that of human IgG with a similar isotype. This approach has been applied to several therapeutically important cytokines, such as IL-2 and IFN-α, and soluble receptors, such as TNF-Rc and IL-5-Rc (see, for example, U.S. Pat. Nos. 5,349,053, 6,224,867 and 7,250,493). In addition, Human NKG2D-Fc chimeric molecules have been described. A human NKG2D-Fc is commercially available (e.g., from R&D Systems) and is used in flow cytometry for detecting NKG2D ligands.

As used herein, NKG2D-Fc is a chimeric molecule comprising at least a portion of the NKG2D receptor fused to an Fc fragment and is capable of binding an NKG2D ligand. The terms "chimera," "chimeric molecule," and the like generally refer to a molecule that is comprised of parts that are from multiple origins or sources. In some embodiments, NKG2D-Fc is produced as a chimeric fusion protein.

NKG2D

NKG2D, also referred to as KLRK1; killer cell lectin-like receptor subfamily K, member 1; CD314; KLR; NKG2-D; FLJ17759; FLJ75772 or D12S2489E, is one of the major triggering receptors of NK cells and is well known in the art. See, for example, Garrity et al. (2005). The portion of the NKG2D receptor used for NKG2D-Fc as described in this disclosure is based on the known sequences of NKG2D (e.g., Accession: NP_031386) or derivatives thereof that bind at least one ligand. As described in more detail herein, derivatives of NKG2D that can be used in the methods of the invention include but are not limited to NKG2D sequences containing one or more mutations, such as a point mutation, a substitution, a deletion mutation and/or an insertion mutation. One of ordinary skill in the art can readily determine suitable derivatives of NKG2D according to the teaching of the present disclosure and knowledge available in the art. At the cDNA level, such a mutation may be a silent mutation. Alternatively, the mutation may result in a change in the corresponding amino acid residue. Where the latter is the case, the change may constitute a conservative change, such that an amino acid residue is replaced with another amino acid residue of similar characteristics. In some cases, however, a mutation may result in a substitution that is non-conservative. Such mutations are acceptable to the extent that the chimeric polypeptide is capable of binding to an NKG2D ligand. More detailed descriptions of different types of NKG2D-Fc chimeras are provided below.

The NKG2D portion of the NKG2D-Fc chimera used for methods provided in this disclosure may be a full length NKG2D polypeptide. The full length sequence of NKG2D has been described in the literature. See, for example, Accession: NP_031386. Additionally, alternative splice variants of NKG2D have been described. For purposes of the instant invention, any one of such alternatively spliced variants may be used, provided that the resulting polypeptide, when constructed as an NKG2D-Fc chimera, is capable of binding its ligans(s).

Alternatively, the NKG2D portion of the NKG2D-Fc chimera used for methods provided in this disclosure may correspond to a partial sequence (i.e., fragment) of the NKG2D receptor polypeptide, provided that the resulting polypeptide, when constructed as an NKG2D-Fc chimera, retains the ability to its ligand(s). For example, the NKG2D portion of the NKG2D-Fc construct may by shortened by either end of the NKG2D sequence by one or more amino acid residues. More specifically, the N-terminus of the NKG2D sequence may be deleted by 1, 2, 3, 4, 5, 6, 7, 8, 9, 10, 11, 12, 13, 14, 15, 16, 17, 18, 19, 20, about 30, about 40, about 50, about 60, about 70, about 80 or more residues. Similarly, the C-terminus of the NKG2D sequence may be deleted by 1, 2, 3, 4, 5, 6, 7, 8, 9, 10, 11, 12, 13, 14, 15, 16, 17, 18, 19, 20 or more residues. In some embodiments, both the N-terminus and the C-terminus may be shortened as described.

It has been shown that the extracellular portion of NKG2D contributes to the formation of homodimers and forms a ligand-binding site(s). Thus, it is possible to delete part or all of the intracellular portion of NKG2D and still maintain the ability to bind its ligand(s). For example, the NKG2D-Fc chimera described in this disclosure may contain predominantly an extracellular fragment of the NKG2D receptor. Structural analyses have revealed that amino acid residues 78 to 216 of the human NKG2D sequence correspond to the extracellular portion of the NKG2D, containing ligand-binding sites. For a murine counterpart, the extracellular domain is amino acid residues 78-232, 94-232 or 92-232.

Accordingly, in some embodiments, the NKG2D-Fc construct comprises the corresponding portion of the NKG2D sequence, e.g., amino acid residues 78-216 of human NKG2D; 78-232, 94-232 or 92-232 of murine NKG2D. In some embodiments, an NKG2D-Fc construct comprises a portion of the extracellular domain. Thus, the extracellular domain of the NKG2D-Fc construct may be shortened at the N-terminus, at the C-terminus, or both. For example, the N-terminus of the extracellular domain used to generate an NKG2D-Fc may be shortened by one or more amino acid residues, e.g., 1, 2, 3, 4, 5, 6, 7, 8, 9, 10, 11, 12, 13, 14, 15, 16, 17, 18, 19, 20, about 30, about 40, about 50, about 60, and so forth, relative to the full extracellular portion of the polypeptide. The C-terminus of the extracellular domain used to generate an NKG2D-Fc may be shortened by one or more amino acid residues, e.g., 1, 2, 3, 4, 5, 6, 7, 8, 9, 10, 11, 12, 13, 14, 15, 16, 17, 18, 19, 20, about 30, about 40, about 50, about 60, and so forth, relative to the full extracellular portion of the polypeptide. Using a human NKG2D as an example, the NKG2D-Fc construct may contain a fragment of the extracellular domain, wherein the N-terminus of the domain begins at amino acid residue 79, 80, 81, 90, 91, 92, 93, 94, 95, 96, 97, 98, 99, 100, about 110, about 120, about 130, about 140 or about 150. Similarly, the NKG2D-Fc construct may contain a fragment of the extracellular domain, wherein the C-terminus of the domain ends at amino acid residue 231, 230, 229, 228, 227, 226, 225, 224, 223, 222, 221, 220, 219, 218, 217, 216, 215, 214, 213, 212, 211, 210, 209, 208, 207, 206, 205, and so forth. Such deletions at each end of the extracellular domain of the NKG2D sequence may be combined.

Also contemplated are NKG2D-Fc derivatives that include one or more mutations in the NKG2D portion of the construct at the interface of the NKG2D-ligand binding. In particular, certain mutations are known to affect the binding affinity between the NKG2D receptor and its ligand such as MICA. See, for example, Lengyel et al., 2007, J. Biol. Chem., 282: 30658-666. The three dimensional structure of a complex between NKG2D and MICA has been described. Accordingly, one of ordinary skill in the art may determine the amino acid residues of NKG2D that contribute to the interaction with its ligand and test the effect of mutations by systematically altering the key residues. In any of the embodiments, the resulting NKG2D-Fc chimera is capable of binding ligand(s). For a comprehensive review of the amino acid residues that are involved in receptor-ligand contact, see, for example, Strong and McFarland, 2004, Advances in Protein Chemistry, 68: 281-213. According to published studies, key residues that are thought to be important in the interaction with the ligand have been mapped to amino acid residues approximately from 150 to 207 in human NKG2D, which correspond to residues approximately from 166 to 223 in mouse NKG2D. Therefore, the NKG2D-Fc construct of the invention preferably comprises a fragment spanning at least most of these residues. Likewise, it will be understood that conservative substitutions, deletions or mutations outside these regions can potentially be tolerated with ease in many instances.

Some amino acid residues have been identified to be especially important for mediating ligand binding. Specifically, residues of human NKG2D important for binding to MICA include Y152, Q185, K197, Y199, E201 and N207. Residues of human NKG2D important for binding to ULBP3 include I182, Y199 and Y152. Residues of murine NKG2D important for binding to RAE-1β include K166, Y168, Y215, K213, E217 and N223. In preferred embodiments, therefore, most or all of these residues (of a corresponding NKG2D construct) are maintained without a mutation or deletion at the position where broad permissibility (e.g., specificity) for multiple ligands is desirable. However, it is also possible to design an NKG2D-Fc construct that preferentially binds one ligand over another ligand by strategically introducing a mutation at one or more of these key residues that confer selective ligand-recognition and binding. On the other hand, certain amino acid residues are involved in the binding of various ligands. For example, Y152 and Y199 in human NKG2D, which are equivalent to Y168 and Y215 respectively in the murine counterpart, contribute to the binding of MICA as well as ULBP3. Therefore, in some embodiments, these residues are unmodified so as to retain broad ligand specificity.

The Examples provided below present a representative NKG2D-Fc chimera, wherein the NKG2D fragment corresponds to amino acid residues 92 to 232 of the murine NKG2D. However, it should be appreciated that the same approach may be employed for NKG2D sequences derived from any other species that are known to develop cancer. For example, the NKG2D fragment of NKG2D-Fc may have 1, 2, 3, 4, 5, 6, 7, 8, 9, 10 or more amino acid changes, such as deletions, insertions and substitutions, as long as the NKG2D-Fc retains its ligand binding activity.

The present invention includes variants of NKG2D-Fc constructs that contain one or more amino acid changes as described above, to the extent that the NKG2D-Fc chimera binds to its native ligand or ligands. To determine whether an NKG2D-Fc variant containing a particular mutation retains ligand binding activity, binding assays can be carried out, in which binding affinity and/or binding capacity of the particular NKG2D-Fc chimera to its ligand(s) may be evaluated. A number of methods are known in the art by which receptor-ligand interactions may be measured. These methods for assaying ligand binding include, without limitation, ELISA, surface plasmon resonance analysis, CD analysis, fluorescence quenching, size-exclusion binding assay and isothermal titration calorimetry. For brief descriptions of these assays, see, for example, Lengyel et al. (2007).

The Fc Fragment

The Fc region of immunoglobulins plays a significant role in mediating immune defense. FcγRs are widely expressed as transmembrane glycoproteins on a number of cell types, including macrophages, NK cells, dendritic cells, B cells, neutrophils and mast cells. Fc-mediated activities include recruitment of effector cells via Fc-FcγR interactions. There are two classes of Fc receptors that can be distinguished functionally: the activating Fc receptor class and the inhibitory Fc receptor class. Activating Fc receptors include human FcγRIA, FcγRIIA and FcγRIIIA, as well as their murine orthologues, i.e., FcγRI, FcγRIII FcγRIV. Activating FcγRs mediate ADCC and ADCP, induce endocytosis of immune complexes leading to antigen presentation, and contribute to the production and release of cytokines and proinflammatory factors. For general review of the IgG structure and mechanisms of action, see Liu et al. (2008; Immunological Reviews, 222: 9-27). As described in more detail herein, the Fc portion of NKG2D-Fc is a domain that binds an activating Fc receptor, and preferably an activating Fc Ig domain and includes the hinge region that allows for dimerization.

The Fc portion of the NKG2D chimera useful for this disclosure can be readily adapted to render it species-specific. For use in a murine system, e.g., cells derived from a mouse, the Fc fragment used to generate NKG2D-Fc is preferably that of a murine origin. In some embodiments, an Fc fragment of the murine IgG2a is preferred. An exemplary chimeric construct containing an Fc region of the murine IgG2a is provided in the Examples.

For use in a human subject, e.g., for cancer treatment, the Fc fragment used to generate NKG2D-Fc is preferably that of a human origin. In particularly preferred embodiments, NKG2D-Fc comprises an activating Fc Ig domain. Among the four human IgG isotypes, an activating Fc domain of $IgG_1$ is preferred for the preparation of NKG2D-Fc.

It has been appreciated in the art that different antibody isotypes have a varying degree of cytotoxic potential in vivo (See, for example, Nimmerjahn F. & Ravetch J V., 2006, Immunity, 24:19-28). For example, the murine IgG2a and IgG2b isotypes are more efficient in clearing infections such as bacterial infections and viral infections and in killing tumor cells than their $IgG_1$ or $IgG_3$ counterparts. This is attributable at least in part to differential ratios of activating versus inhibitory FcRs present in vivo. Similarly, with respect to human IgG isotypes, $IgG_1$ and $IgG_3$ have a stronger interaction with FcRs than $IgG_2$ or $IgG_4$. Moreover, certain polymorphic allotypes of a given isotype may influence affinity for an Fc receptor. Indeed, there are allelic variants of activating FcRs that will significantly affect the affinity for certain antibody isotypes. For example, the FcγRIIIa receptor 158V allotype displays a higher affinity for human immunoglobulin $G_1$ and increased antibody-dependent cellular cytotoxicity (Cartron G. et al., 2002, Blood, 99: 754-758).

Thus, as shall be clear to the skilled artisan, it is possible to optimize the interaction between the Fc portion of the NKG2D-Fc chimera to its corresponding Fc receptor by strategically selecting or modifying the Fc allele used for preparing the NKG2D-Fc chimera. Accordingly, the invention contemplates using a mutant or an allotype of an Fc fragment. A number of useful mutations within an Fc domain have been described, which can affect the interaction of an Fc and its receptor, the effector function of the Fc, as well as the half life of the Fc-containing molecule. These include specific amino acid substitutions and/or modifications to carbohydrate moieties in the Fc. For review, see, for example, Liu et al., 2008, Immunological Reviews, 222:9-27; Nimmerjahn & Ravetch, 2007, Curr. Opin. Immunol., 19(2): 239-45.

As described herein, the NKG2D-Fc chimera useful for the methods provided in this disclosure contains an Fc portion. The structure of Fc fragments generally is known in the art. Briefly, the Fc region of a typical IgG molecule is a symmetric homodimer of the carboxy-terminal portion of heavy chains and is composed of the $C_H2$ and $C_H3$ domains, which are separated from the Fab by a flexible hinge region. The Fc region is stabilized by non-covalent interactions between domains. The Fc region interacts with FcRs to exert effector functions or to regulate the catabolism of IgG. The heavy constant regions ($C\gamma_2$ and $C\gamma_3$) and the hinge region located between the variable domain and the constant regions interact with Clq and Fc receptors (FcRs). Thus, the heavy constant regions of the IgG molecule are responsible for its effector functions, since they include binding sites for complement and for FcRs on different effector cells. Recruitment of effector cells is therefore mediated via the Fc-FcγR interactions.

In general, the interaction of an antibody with complement initiates complement-dependent cytotoxicity (CDC), and FcγR interactions mediate antibody-dependent cell toxicity (ADCC) and antibody-dependent cell phagocytosis (ADCP). The classical activation pathway of CDC is triggered when C1, the first component of the pathway, binds to the hinge-Fc portion of the IgG in an antigen-antibody complex. Subsequent activation of the complement cascades eventually induces the formation of a C5-C9 membrane attack complex that leads to the death of the target cell. ADCC, on the other hand, is dependent upon the ability of the FcγR-bearing cells of the innate immune system (e.g., NK cells, monocytes, macrophages and granulocytes) to recognize the Fc domain of antibody bound to target cells. This recognition triggers effector cells to release cytoplasmic perforin, granulysin, and granzymes that induce apoptosis and lysis of target cells. The major effector cells in ADCC are NK cells, which express the type of FcγRs that recognize the IgG1 and IgG3 subclasses and trigger cytotoxic effects in vivo.

In the context of the present invention, as demonstrated in the Examples, the NKG2D-Fc chimeras described herein are capable of mediating equivalent cellular effects by virtue of having a functional Fc portion, coupled with the NKG2D portion that can broadly but specifically recognize and bind to its ligands.

As noted, there are activating receptors (FcγRI, FcγRIIA and FcγRIII) and inhibitory (FcγRIIB) receptors. In general, interaction of IgGs with activating FcγRs triggers cell activation, while interaction with FcγRIIB inhibits cell activation. With the exception of B cells and NK cells, activating and inhibitory FcγRs are co-expressed on the same effector cells, thereby generating a threshold for cell activation. B cells express only the inhibitory FcγRIIB and therefore cannot be activated by endogenous IgG under physiological conditions. NK cells express the activating FcγRIII so that they can kill target cells independently of preactivation (or priming).

FcγRIIA and FcγRIII (CD16) have low affinities for monomeric IgG and are thought to be critical for triggering effector functions, leading to anti-tumor activity. Thus, it is possible to design an NKG2D-Fc such that it is genetically engineered to have increased affinities for the activating FcγRIII, and decreased affinities for the inhibitory FcγRIIB.

Accordingly, the amino acid residues of NKG2D-Fc molecules that contribute to their direct interaction with FcγRs, which are located primarily in the lower hinge region and are adjacent to the Cγ2 region, may be modified, and such variants are embraced by this invention. It has been shown that the region corresponding to amino acid residues 234-237 of the IgG is required for binding to FcγRs. In addition, other residues that are important in IgG-FcγRs interactions have been shown to be located in the Cγ2 domain and include Asp265, Asp270, Ala327, Pro329 and Lys338.

Several strategies are contemplated to generate NKG2D-Fc chimeras with enhanced activities. To engineer the NKG2D-Fc with an enhanced ADCC capability, at least two approaches are contemplated. First, based on the amino acid residues in an IgG1 that were identified to be critical for its binding to activating and inhibitory FcγRs, the invention provides variants of NKG2D-Fc chimeras that enhance or reduce, respectively, the affinity for these receptors. Accordingly, in one embodiment, the triple amino acid substitution, Ser298Ala/Glu333Ala/Lys334Ala, where the position of each residue is based on IgG1, is provided. The NKG2D-Fc containing this triple mutation should exhibit a higher affinity for FcγRIIIA but not for FcγRIIB, thereby promoting ADCC. Similarly, in another embodiment, the NKG2D-Fc variant contains the double mutation in the Fc, Ser239Asp/Ile332Glu, which is expected to exert improved ADCC. Other mutations for enhancing ADCC include, without limitation, Ser239Asp/Ala330Leu/Ile332Glu and Ser239Asp/Ser298Ala/Ile332Ala. Similarly, in some embodiments, mutations that combine increased binding to FcγRIIIA (e.g., activating receptors) and reduced binding to FcγRIIB are contemplated. Examples of such Fc mutations include Phe243Leu/Arg292Pro/Tyr300Leu/Val305Ile/Pro396Leu, without limitation (the positions of the residues are based on IgG1).

The second approach relates to modifying the carbohydrate moieties in the Fc based on the observation that some modifications significantly affect the affinity of the Fc for FcγRs. It has been shown that the Fc domain contains two asparagine N-linked oligosaccharide sites (Reviewed in Liu et al., 2008). ADCC requires the presence of certain oligosaccharides and is dependent upon changes in the structure of the oligosaccharides. In particular, previous studies have shown that removing the fucose moiety attached to the innermost GlcNAc of the biantennary complex-type oligosaccharides dramatically increases ADCC by improving the binding of the Fc to FcγRIIIA without impairing CDC activity. Based on this observation, in one embodiment, the invention provides fucose-deficient NKG2D-Fc. In some embodiments, the chimera completely lacks the fucose moiety (i.e., non-fucosylated). In other embodiments, the chimera is hypofucosylated.

To make NKG2D-Fc containing modified carbohydrates, host cells may be engineered to express the enzymes that catalyze the desired modification(s). For example, host cells, such as Chinese hamster ovary (CHO) cells may be transfected with the enzyme, β-(1,4)—N-acetylglucosaminyltransferase III (GnT-III), which elevates the level of bisected, non-fucosylated oligosaccharides. The NKG2D-Fc product generated from these host cells can have a dramatically enhanced ADCC activity. In addition, in some embodiments, the content of fucose in NKG2D-Fc may be manipulated by α-1,6-fucosyltranfesafe (FUT8)-knockout cells lacking core-fucosyl transferase activity. Alternatively, small interfering RNA may be used to constitutively inhibit the expression of the FUT8 enzyme to achieve the same effect. In some embodiments, host cells deficient in guanosine diphosphate (GDP)-mannose 4,6-dehydratase (GMD) may be used to yield non-fucosylated NKG2D-Fc.

Next, to engineer the NKG2D-Fc with an enhanced complement activity, various mutations in the Fc domain are contemplated. Generally, complement can be activated by at least three pathways, leading to the formation of the membrane attach complex C5b-9, which forms pores in the plasma membranes of target cells and causes their lysis. C1q binding to the Fc domain is a critical step in this process. Among the human IgG subclasses, only IgG1 and IgG3 can initiate the complement cascade. In some embodiments, mutations are introduced to the Fc domain of the NKG2D-Fc, so as to promote C1q recruitment and the C1q-Fc interaction. The residues of the Fc targeted for such mutations include, but are not limited to: Asp270, Lys322, Pro329 and Pro331. These mutations involve substituting the corresponding residue(s) with nonpolar neutral amino acids, such as Ala, Met, or Trp. In a specific embodiment, the NKG2D-Fc contains the mutation, Lys326Trp, Glu333Ser or both.

To achieve increased C1q binding and enhanced CDC, some embodiments of the invention involve introducing a mutation or mutations to certain residues of the hinge region of human IgG1. Non-limiting examples of such mutations include: Lys222Trp/Thr223Trp, Cys220Asp/Asp221Cys, Cys220Asp/Asp221Cys/Lys222Trp/Thr223Trp, Lys222Trp/Thr223Trp/His224Trp and Asp221Trp/Lys222Trp.

In addition, it should be noted that when fusion proteins with artificial sequences and activities are used as therapeutic agents, in some circumstances, patients treated with such a fusion protein trigger an unwanted immune response, such as development of antibodies against the agent. Certain structural modifications of an Fc fragment have been shown to reduce immunogenicity of a therapeutic fusion protein. See, for example, U.S. Pat. No. 6,992,174 B2 by Gillies et al., which is incorporated by reference herein; Liu et al., 2008, Immunological Reviews, 222:9-27. Such modifications may be useful for an effective design of NKG2D-Fc described in the present disclosure.

Linkers

The NKG2D-Fc construct used in the methods of the present disclosure may comprise a linking moiety that connects a NKG2D portion with an Fc fragment. In some cases, a hinge region of Fc fusion protein molecules serves as a spacer between the Fc region and the fused peptide (e.g., soluble receptor), allowing these two parts of the molecule to function separately (see, for example, Ashkenazi et al., 1997).

In some embodiments, an Fc portion and an NKG2D portion that comprise a chimeric molecule are linked via a linking molecule which is not a contiguous portion of either NKG2D or Fc and which covalently joins an amino acid of NKG2D to an amino acid of Fc. As used herein, a linking molecule that is "not a contiguous portion" means that the NKG2D portion and the Fc portion of the chimera are connected via an additional element that is not a part of the NKG2D or immunoglobulin that is contiguous in nature with either of the chimeric portions and functions as a linker. Non-limiting examples of a linking molecule that is not a contiguous portion of either NKG2D or Fc are described below.

The linking molecule may be a peptide linker. Where the linker is a peptide linker, the NKG2D-Fc chimera may be produced as a single recombinant polypeptide using a conventional molecular biological/recombinant DNA method.

In some embodiments, a peptide linker provides a protease-dependent cleavable site. Examples of protease-cleavable peptide linkers include, without limitation, the MMP sensitive linker GGPLGLWAGG (SEQ ID NO: 2) and the factor Xa-sensitive linker IEGR (SEQ ID NO: 1). The art is familiar with a variety of cleavable sequences that may be employed for the methods provided herein.

In some embodiments of the present invention, a flexible peptide linker is used. A flexible peptide linker is preferably about 20 or fewer amino acids in length. More preferably, a peptide linker contains about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

In some embodiments, the NKG2D-Fc chimera contains an IEGR (SEQ ID NO: 1) peptide linker.

Alternatively, a linking molecule may be a non-peptide linker. As used herein, a non-peptide linker useful for the method provided in the present disclosure is a biocompatible polymer including two or more repeating units linked to each other. Examples of the non-peptide polymer include but are not limited to: polyethylene glycol (PEG), polypropylene glycol (PPG), co-poly (ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, and heparin. For more detailed descriptions of non-peptide linkers useful for Fc fusion molecules, see, for example, WO/2006/107124, which is incorporated by reference herein. Typically such linkers will have a range of molecular weight of from about 1 kDa to 50 kDa, depending upon a particular linker. For example, a typical PEG has a molecular weight of about 1 to 5 kDa, and polyethylene glycol has a molecular weight of about 5 kDa to 50 kDa, and more preferably about 10 kDa to 40 kDa.

Other Moieties

In some embodiments, NKG2D-Fc chimeras useful for the methods described herein may further comprise one or more accessory moieties, such as a tag sequence and a signal sequence. For example, a tag sequence can be used for detecting and/or isolating the polypeptide. Examples of tags include, without limitation: HA, Flag, Myc, Glu, His6x and Maltose basic protein. The tag sequence may be located at the amino terminus, carboxyl terminus, or located somewhere in the middle of the NKG2D-Fc chimeric molecule (e.g., between modular peptide fragments), provided that the presence of such a tag does not interfere with the function of the NKG2D-Fc molecule.

In some cases, a tag sequence is cleavable.

In some embodiments, NKG2D-Fc chimeras may optionally comprise a signal sequence. A signal sequence is a short (typically about 3-60 amino acids long) peptide chain that directs the post-translational transport of a polypeptide, thereby allowing a greater yield of the polypeptide. The amino acid sequences of a signal sequence direct polypeptides (which are synthesized in the cytosol) to certain subcellular compartments, e.g., organelles. A signal sequence is also referred to as a targeting signal, a signal peptide, a transit peptide, or a localization signal. In some embodiments, a signal sequence is cleaved from the polypeptide by signal peptidase after the polypeptide is transported.

In some embodiments, the NKG2D chimera contains an N-terminal modified IL-2 signal sequence, which allows for optimal expression and secretion of NKG2D-Fc construct. See, for example, Zhang et al., 2004, J. Gene Med., 7:354-65. In some embodiments, the NKG2D chimera contains a signal peptide derived from the polypeptide sequence of CD33. For example, the CD33 signal peptide may correspond to amino acid residues 1-16 of the CD33 polypeptide sequence. One of ordinary skill in the art will understand that there are a number of other suitable signal peptide sequences that may be used to practice the methods provided in this disclosure. In addition, where there is a signal peptide present in the NKG2D chimera, extra amino acid residues, e.g., a spacer, may be optionally inserted between the N-terminus signal peptide and the Fc portion of the chimera. In some embodiments, for example, a signal sequence is followed by a Met-Asp dipeptide spacer.

It should be appreciated that the NKG2D-Fc chimeras as described herein can be designed to carry "payloads," such as drugs (e.g., small molecules), toxins, radionuclides, enzymes and/or cytokins to cancer cells.

Exemplary NKG2D-Fc constructs

Accordingly, in some embodiments, the present disclosure provides methods for treating cancer in a subject using NKG2D-Fc, wherein the NKG2D portion of the chimeric molecule comprises an extracellular domain of the NKG2D receptor, corresponding to so-called a C-type lectin-like domain (which corresponds to amino acid residues F92 through V232 in human NKG2D), linked via a peptide linker, to an activating Fc Ig domain derived from human IgG1. The peptide linker is in some cases an IEGR (SEQ ID NO: 1) linker. In some embodiments, the NKG2D-Fc chimera further comprises a signal sequence to enhance expression and trafficking (such as secretion) of the NKG2D polypeptide.

The Examples provided below describe a murine counterpart of the NKG2D-Fc chimera. In particular, an exemplary NKG2D chimera is described that contains the $C_H2$ and $C_H3$ domains of murine IgG2a. The $C_H2$ and $C_H3$ domains of murine IgG2a allows complement fixation and Fc receptor binding for opsonization and antibody dependent cellular cytotoxicity (ADCC).

More specifically, the murine NKG2D-Fc chimera comprises a murine IgG2a Fc fragment, fused to an extracellular portion of the murine NKG2D, corresponding to amino acid residues F78 through V232, wherein the Fc fragment and the NKG2D fragment are linked via an IEGR (SEQ ID NO: 1) peptide linker. In a preferred embodiment, the NKG2D-Fc chimera comprises an N-terminal modified IL-2 signal sequence to allow enhanced expression and secretion of the recombinant construct. Murine NKG2D-Fc molecules are useful for studying cancer in mouse models.

The NKG2D receptor is known to form a homodimer. The dimerized complex is shown to be the functional form of the receptor, which binds a single ligand. A recombinant NKG2D-Fc molecule described herein can form a dimer by virtue of the hinge region of the Fc fragment that mediates dimer formation by disulfide bonding. In certain circumstances, however, a region of the NKG2D portion of the NKG2D-Fc chimera may also contribute to dimerization.

Preparation of NKG2D-Fc

The art is familiar with molecular biological and biochemical techniques for preparing an NKG2D-Fc chimera with desired features. Preferably, NKG2D-Fc chimeric constructs are produced by conventional recombinatory DNA methods. In preferred embodiments, an NKG2D-Fc chimera is produced as a single (e.g., contiguous) recombinant polypeptide. In other embodiments, two or more portions of NKG2D-Fc are produced as separate fragments and are subsequently linked together to yield an NKG2D-Fc molecule. For example, an NKG2D portion of the NKG2D-Fc and an Fc portion of the NKG2D-Fc are each produced as separate recombinant polypeptides then fused together by a chemical linking means to yield NKG2D-Fc. This production methodology may be preferred particularly in situations where a non-peptide linking molecule is employed. Similarly, this production methodology may be also preferred if a chimeric NKG2D-Fc does not fold correctly (e.g., does not properly bind a ligand) when made as a single contiguous polypeptide.

For the production of recombinant polypeptides, a variety of host organisms may be used. Suitable hosts include, but are not limited to: bacteria such as *E. coli*, yeast cells, insect cells, plant cells and mammalian cells. Choice of a suitable host organism will depend on the particular application of the NKG2D-Fc chimera. The skilled artisan will understand how to take into consideration certain criteria in selecting a suitable host for producing the recombinant polypeptide. Factors affecting selection of a suitable host include, for example, post-translational modifications, such as phosphorylation and glycosylation patterns, as well as technical factors, such as the general expected yield and the ease of purification. Host-specific post-translational modifications of an NKG2D-Fc, which is to be used in vivo, should be carefully considered because certain post-specific modifications are known to be highly immunogenic (antigenic).

Once produced, NKG2D-Fc can be purified by any suitable means such as chromatographic methods known to those of skill in the art. Examples of chromatographic methods include gel filtration chromatography. See, for example, Caine et al., Protein Expr. Purif., 1996, 8:159-66.

As will be recognized by one of ordinary skill in the art, the two chimera portions also can be prepared and isolated separately and joined by chemical synthesis.

NKG2D Receptor Ligands

In any of the embodiments described in this disclosure, NKG2D-Fc is capable of binding the endogenous ligand of the NKG2D receptor. Known NKG2D-ligands in humans include MICA, MICB, RAET-1G, ULBP1, ULBP2, ULBP3 and ULBP4. Preferably, the NKG2D-Fc chimera descried in the present disclosure is capable of binding more than one type of NKG2D receptor ligand.

In some embodiments, the NKG2D-Fc chimeric molecules bind ligands with high affinity of $10^{-4}$ or less, $10^{-7}$M or less, or with subnanomolar affinity, e.g., 0.9, 0.8, 0.7, 0.6, 0.5, 0.4, 0.3, 0.2, 0.1 nM or even less. In some embodiments, the binding affinity of the NKG2D-Fc molecule for its ligands is at least $5\times10^6$ Ka, at least $1\times10^7$ Ka, at least $2\times10^7$ Ka, at least $1\times10^8$ Ka, or greater.

In some embodiments, NKG2D-Fc binds preferentially to (e.g., with higher affinity for) a subset of NKG2D receptor ligands. 3D structural data in combination with mutagenesis analyses have revealed that NKG2D is permissive in the recognition and binding of a diverse array of its endogenous ligands. More detailed descriptions regarding the specific residues involved in the receptor-ligand interaction are provided elsewhere herein.

A ligand for NKG2D may be expressed on a cell surface. Alternatively, a ligand for NKG2D may be "shed" from the cell surface and is present as a soluble ligand. It has been known in certain cancers that NKG2D ligands such as MICA are over-expressed and in some cases released (e.g., shed) into the bloodstream or surrounding tissues in a soluble form, e.g., in sera. It is believed that this contributes, at least in part, to the pathogenesis and/or progression of cancer. Thus, the NKG2D-Fc is useful for binding such ligand, either present on cell surface or as a released form, in counterbalancing the expression of the ligands that are present at an abnormally elevated level by functioning as a neutralizing agent.

Where an NKG2D ligand is expressed on the surface of cancer cells of a subject, NKG2D-Fc described in the present disclosure binds to the cell surface ligand when administered to the subject. The binding of the NKG2D-Fc chimera to its ligand may prevent activation of endogenous NKG2D receptors present on NK cells.

Where an NKG2D ligand is "shed" from cancer cells, i.e., released into the bloodstream of a subject, NKG2D-Fc described herein binds to the soluble ligand, sequestering it from further action.

As described in more detail in the Examples, a murine NKG2D-Fc chimera binds both recombinant soluble NKG2D ligands in an ELISA and native ligands expressed on the tumor cell surface. Data are provided herein to show that the NKG2D-Fc chimera mediates potent and specific complement dependent lysis, antibody-dependent cellular cytotoxicity, and efficient opsonization of NKG2D ligand-expressing tumor cells.

Therapeutic Applications

Normally, expression of the NKG2D ligands appears to be confined to the gastrointestinal epithelium. Little expression is observed in quiescent epithelial cells, but higher levels of expression occur in rapidly proliferating cells. Expression of the NKG2D ligands is also up-regulated in various transformed cells, particularly those of epithelial origin. Accordingly, provided herein are methods for treating cancer or symptoms of cancer in a subject. The methods comprise administering to the subject a therapeutically effective amount of NKG2D-Fc that binds NKG2D ligands in vivo.

The terms "treating" "treatment" and "treat" and the like in the context of a cancer therapy refer to the administration of a composition comprising NKG2D-Fc as described herein to a subject who has cancer. The composition is administered to the subject in an amount that is therapeutically effective. As used herein, a therapeutically effective amount refers to an amount of the therapeutic that is believed to effectuate a beneficial effect with statistical significance on the subject having the disease or disorder, such as certain types of cancer. Generally, a therapeutically effective amount is determined by administering the composition to a population of subjects with specified conditions (such as progression or stage of a disease) and evaluating the outcome in response. As used herein, therapeutic treatment shall include, for example, complete prevention or abolishment of the symptoms of a disease, a delay in onset of the symptoms of a disease, or lessening in the severity of a disease.

Cancer

Cancer broadly refers to a proliferative disease involving transformed cells, including both pre-malignant and malignant disorders. The present invention is useful for treating a subject having cancer that is characterized by over-expression of one or more NKG2D ligands. In some embodiments, the cancer is characterized by over-expression of one (or predominantly one) ligand of the NKG2D receptor. In other embodiments, the cancer is characterized by over-expression of two or more NKG2D ligands.

The methods disclosed herein are useful therapeutics for the treatment of pre-malignant disorders that carry with them a risk of progressing to malignancy. Examples of such disorders include, without limitation, dysplasia, hyperplasia, and plasma cell disorders such as monoclonal gammopathy of undetermined significance (MGUS) and smoldering multiple myeloma (SMM). In some embodiments, the cancer is melanoma, lung, breast, kidney, ovarian, prostate, pancreatic, gastric, and colon carcinoma, lymphoma or leukemia. In some embodiments, the cancer is melanoma. In some embodiments, the cancer is a plasma cell malignancy, for example, multiple myeloma (MM) or pre-malignant condition of plasma cells. In some embodiments, the subject has been diagnosed as having a cancer or as being predisposed to cancer. Thus, methods disclosed herein are also useful to treat a subject who has had a metastasis and is therefore susceptible to a relapse or recurrence. The methods are particularly useful in high-risk individuals who, for example, have a family history of cancer or metastasizing tumors, or show a genetic predispositions for a cancer metastasis. Specifically, the methods are directed to treating cancer that is associated with NKG2D ligand expression. In some embodiments, an NKG2D ligand is MICA. Thus, in some embodiments, the cancer causes MICA-related tumors.

Whether a particular subject (e.g., patient) should receive a cancer therapy comprising NKG2D-Fc can be determined by testing for aberrant expression of one or more NKG2D ligands in the subject. "Aberrant expression of one or more NKG2D ligands" in the subject means over-expression of the ligand(s) in a biological sample obtained from the subject. In some embodiments, a biological sample may include a biopsy sample taken from a tissue of the subject suspected to be cancerous. For example, in some cases, a biological sample is collected from a solid tumor to test for malignancy. In other cases, a biological sample may constitute a blood sample, e.g., serum, a stool sample, urine sample, etc. A biological sample may be any cell or tissue sample that is collected from a subject for the purpose of testing for the diagnosis or progression of a disease, such as cancer.

One of ordinary skill in the art is familiar with a variety of laboratory techniques and protocols used to assay for the presence of and the levels of one or more markers present in a biological sample. To determine whether a subject has cancer that is associated with over-expression of NKG2D ligand(s), typically immunoaffinity assays are performed. In certain situations, depending on the type of biological samples that are available, immunohistological or immunocytochemical analyses may be carried out. A number of antibodies are commercially available for performing these analyses. Methods commonly employed for this purpose include, but are not limited to, ELISA, immunoblotting, and immunohistochemistry.

Subjects

The methods disclosed herein can be applied to a wide range of species, e.g., humans, non-human primates (e g, monkeys), horses, cattle, pigs, sheep, deer, elk, goats, dogs, cats, mustehds, rabbits, guinea pigs, hamsters, rats, and mice, which are known to develop cancer. Thus, a "subject" as used herein is a mammalian subject having a disease, or at risk of developing a disease associated with an abnormal expression of at least one NKG2D ligand, such as cancer. In preferred embodiments, the subject is a human subject having a cancer presenting elevated levels of one or more NKG2D ligands. In some embodiments, the NKG2D ligands include MICA.

If a subject has been shown to express an elevated level of one or more NKG2D ligands, the subject may be treated with the methods described herein. In some circumstances, a subject has received or is receiving another cancer therapy. In some embodiments, the cancer may be in remission. In some cases, the subject is at risk of having recurrence, e.g., metastasis. In some embodiments, the over-expression of one or more NKG2D ligands is limited to cancerous cells, e.g., tumors. In some embodiments, at least one of the NKG2D ligands expressed by cancer cells are shed into the blood stream, and thus detectable in the serum of the subject.

Depending on the phenotype of a particular cancer, it may be possible to target one or more ligands which are over-expressed (expressed by tumor cells) over the other ligands, whose expression is not significantly affected.

Modes of Action

Without being limited by any particular theory, it appears that NKG2D-Fc chimeras can function through the two major components of the immune system: the innate immunity and adaptive immunity. As used herein, innate immunity or the innate immune system refers to non-specific host defense mechanisms against foreign pathogens. Innate immunity includes both physical barriers (e.g., skin, gastric acid, mucus or tears, as well as cells and active mechanisms such as NK cells, phagocytes and the complement system.

NK cells represent a major component of the innate immune system. NK cells are cytotoxic, e.g., are able to attack cells that have been infected by microbes, as well as some kinds of tumor cells. The cytotoxic activity of NK cells is mediated through cell-surface receptors that recognize MHC class I alleles. A number of receptor types are known in the art, including NKG2D, which is one receptor subtype. Phagocytic cells include neutrophils, monocytes, macrophages, basophils and eosinophils. The complement system is a biochemical cascade of the immune system that helps clear pathogens from a host organism.

In general, adaptive immunity or the adaptive immune system refers to an antigen-specific antibody-mediated immune response. Adaptive immunity is generally mediated via specific antibody production by B lymphocytes and antigen-specific activity of T lymphocytes. The humoral response mediated by B lymphocytes defends primarily against extracellular pathogens through the production of circulating antibodies that mark foreign cells and molecules for destruction by other specialized cells and proteins. The cellular response mediated by T lymphocytes defends predominantly against intracellular pathogens and cancer cells by directly binding to and destroying the affected cells. According to the present disclosure, NKG2D-Fc, which is a non-antibody molecule, is believed to functionally mimic what is ordinarily the function of specific antibodies.

The present invention thus contemplates methods for cancer treatment, wherein NKG2D-Fc binds directly to tumor cells that are expressing NKG2D ligands on the cell surface. In this mode of action, NKG2D-Fc can specifically identify for destruction of tumor cells that over-express NKG2D ligands, but not healthy cells that do not.

As shown in the Examples, it has been discovered that NKG2D-Fc can target any or all NKG2D ligands that are expressed on human tumor cells in at least two ways. One mechanism of mediating tumor cell destruction is through the process of complement lysis (also referred to as complement dependent lysis, complement-dependent cytotoxicity or CDC). A second way of mediating tumor cell destruction is by triggering antibody dependent cellular cytotoxicity (ADCC).

In some embodiments, NKG2D-Fc acts as an opsonizing agent. Opsonization is the process where cells or particles become coated with molecules which allow them to bind to receptors on other cells, such as dendritic cells or phagocytes, to promote the uptake. For antigen-presenting cells such as dendritic cells and macrophages, opsonization promotes efficient processing and presentation of antigens. Opsonizing agents that are capable of specifically binding to both the target (e.g., ligands) and particular receptors on antigen-presenting cells (e.g., FcRs) that can mediate internalization and subsequent antigen processing are particularly useful.

Tumor cells that express one or more ligands of the NKG2D receptor on the cell surface can become opsonized, e.g., coated, with NKG2D-Fc molecules. For example, the NKG2D portion of the chimera can bind to the ligands on the tumor cell surface, while leaving the Fc portion of the chimera exposed. Dendritic cells have FcγRs and therefore can bind to and internalize the tumor antigen (e.g., NKG2D ligands), which then results in antigen presentation to cytotoxic T cells, also known as CD8+ T cells. This is referred to as cross-priming. Similarly, opsonization results in the generation of MHC class II-restricted CD4+ T cell responses. Through opsonization, therefore, the NKG2D-Fc chimera can promote efficient cross-presentation (e.g., priming) by dendritic cells, leading to the induction of potent T cell responses against the tumor.

Cancer patients often suffer from immune suppression. In some cases, it is believed that the immune suppression, at least in part, may be caused by impaired NKG2D receptor signaling. Based on a prevailing model, for example, shed MICA impairs host defense by inducing the internalization of NKG2D receptor molecules on lymphocytes. Thus, according to this model, tumor cell shedding of MICA results in immune suppression through down-regulation of NKG2D surface expression.

Therefore, the methods provided herein are useful for counteracting or relieving immune suppression by administering a composition comprising NKG2D-Fc, particularly in situations where a patient exhibits elevated levels of soluble (i.e., shed) NKG2D ligand or ligands that are detectable in sera. The mode of action is that NKG2D-Fc administered to the patient binds to (thus sequestering) excess soluble ligands of NKG2D that were shed from tumors, thereby reversing the down-expression of NKG2D receptors on cell surface that led to immune suppression.

Thus, the NKG2D-Fc chimera can have multiple therapeutic functions, including neutralizing soluble ligands that are shed by tumor cells, promoting ADCC and/or CDC in tumor cells expressing the cell surface ligands and mediating cross presentation and priming of the adaptive immune system, including CD8 cytotoxic T-lymphocytes (CTLs) and tumor-specific antibody producing B-cells.

Administration

The NKG2D-Fc composition can be administered directly to a subject. The subject is preferably a mammal. The terms "administration" and "administer" refer to a means of providing a pharmaceutical agent to a subject such that the pharmaceutical agent is to contact its target cells, e.g., cancer cells, in vivo, i.e., in the body of the subject. In some embodiments, the composition comprising NKG2D-Fc is systematically administered to a subject. In preferred embodiments, a systematic administration is delivered via an intravenous injection. In some embodiments, the composition comprising NKG2D-Fc is administered locally. For example, in some cases, the composition may be delivered directly to or within close proximity of a solid tumor.

Pharmaceutically-Acceptable Carriers

Generally, the composition comprising NKG2D-Fc can be suspended in a pharmaceutically-acceptable carrier (e.g., physiological saline). Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters, for example. Aqueous earners include, without limitation, water, alcohol, saline, and buffered solutions. Preservatives, flavorings, and other additives such as, for example, antimicrobials, antioxidants, chelating agents, inert gases, and the like also may be present. It will be appreciated that any matenal described herein that is to be administered to a mammal can contain one or more pharmaceutically acceptable carriers.

Routes of Administration

Any composition described herein can be administered to any part of the subject's body via various administration routes. The composition can be administered by intravenous, intraperitoneal, intramuscular, subcutaneous, intramuscular, intrarectal, mtravaginal, intrathecal, intratracheal, intradermal, or transdermal injection, by oral or nasal administration, by inhalation, or by gradual perfusion over time. The composition can be delivered to specific tissue. For example, the composition can be delivered to, without limitation, the joints, nasal mucosa, blood, lungs, intestines, muscle tissues, skin, or peritoneal cavity of a mammal. In a further example, an aerosol preparation of a composition can be given to a host by inhalation.

Dosage

The dosage required depends on the route of administration, the nature of the formulation, the nature of the patient's illness, the subject's size, weight, surface area, age, and sex, other drugs being administered, and the judgment of the attending physician. Suitable dosages are typically in the range of 0.01-1,000 μg/kg. Wide variations in the needed dosage are to be expected in view of the variety of NKG2D-Fc compositions available and the differing efficiencies of various routes of administration. Variations in these dosage levels can be adjusted using standard empirical routines for optimization as is well understood in the art. Administrations can be single or multiple (e.g., 2- or 3-, 4-, 6-, 8-, 10-, 20-, 50-, 100, 150-, or more fold). Encapsulation of the composition in a suitable delivery vehicle (e.g., polymeric microparticles or implantable devices) may increase the efficiency of delivery.

Treatment Regimen

The duration of treatment with any composition provided herein can be any length of time from as short as one day to as long as the life span of the host (e.g., many years). For example, NKG2D-Fc compositions can be administered once a month for three months or once a year for a period often years. It is also noted that the frequency of treatment can be variable. For example, NKG2D-Fc compositions can be administered once (or twice, three times, etc.) daily, weekly, monthly, or yearly. NKG2D-Fc compositions can be administered together, i.e., at the same point in time or sequentially, with one or more other cancer therapies. For example, a patient can receive an autologous tumor cell vaccine followed by an anti-CTL4 antibody, followed by an NKG2D-Fc therapy, separated by intervals of hours, days, months or years.

Adjuvant

The compositions can be administered along with an adjuvant. An "adjuvant" is an immunological compound that can enhance an immune response against a particular antigen such as a polypeptide. Examples of adjuvants include alum and other aluminum-based compounds (e.g., $Al_2O_3$). Aluminum-based compounds can be obtained from various commercial suppliers. Other adjuvants include immunostimulating complexes (ISCOMs) that can contain such components as cholesterol and saponins, one or more additional immunostimulatory components, including, without limitation, muramyldipeptide (e.g., N-acetylmuramyl-L-alanyl-D-isoglutamme, MDP), monophosphoryl-lipid A (MPL), and formyl-methionme containing tripeptides such as N-formyl-Met-Leu-Phe. Such compounds are commercially available from Sigma Chemical Co (St Louis, Mo.) and RIBI is ImmunoChem Research, Inc (Hamilton, Mont.), for example. Other adjuvants can include CpG oligodeoxynucleotides (Coley Pharmaceuticals), QS21 (Cambridge Biotech) and MF59 (Chiron) Adjuvants that enhance dendπtic cell function can also be used, examples include GM-CSF, FH3-ligand, and interferons.

The NKG2D-Fc compositions described herein can contain any ratio of adjuvant to NKG2D-Fc. The adjuvant/NKG2D-Fc ratio can be 50:50 (vol:vol), for example. Alternatively, the adjuvant/NKG2D-Fc ratio can be, without limitation, 99:1, 90:10, 80:20, 70:30, 64:36, 60:40, 55:45, 40:60, 30:70, 20:80, 90:10 or 1:99.

Effective Amounts

An effective amount of any composition described herein can be administered to a subject. The term "effective" as used herein refers to any amount that induces a desired therapeutic effect, such as an immune response, while not inducing significant toxicity in the subject. Such an amount can be determined by assessing a subject's biological reaction, e.g., immune response and improvement in a symptom, after administration of a known amount of a particular composition. In addition, the level of toxicity, if any, can be determined by assessing a subject's clinical symptoms before and after administering a known amount of a particular composition. It is noted that the effective amount of a particular composition administered to a subject can be adjusted according to a desired outcome as well as the host's response and level of toxicity. Significant toxicity can vary for each particular host and depends on multiple factors including, without limitation, the subject's disease state, age, and tolerance to pain.

Combination Therapy

In some cases, the subject in need of cancer treatment is treated with the NKG2D-Fc composition described herein in conjunction with additional cancer therapy. In some embodiments, the additional cancer therapy includes a cytotoxic agent and/or non-cytotoxic agent. A "cytotoxic agent" refers to a substance that inhibits or prevents the function of cells and/or causes destruction of cells. The term is intended to include radioactive isotopes (e.g., $^{131}$I, $^{125}$I, $^{90}$Y and $^{186}$Re), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A "non-cytotoxic agent" may include an agent that can be activated to be cytotoxic. A non-cytotoxic agent may include a bead, liposome, matrix or particle (see, e.g., U.S. Patent Publications 2003/0028071 and 2003/0032995, which are incorporated by reference herein). Such agents may be conjugated, coupled, linked or associated with an NKG2D-Fc composition described herein.

In some embodiments, conventional cancer medicaments are administered with the compositions described herein. In some cases, the subject in need of cancer treatment is treated with the NKG2D-Fc composition described herein in conjunction with one or more additional agents directed to target cancer cells. Highly suitable agents include those agents that promote DNA-damage, e.g., double stranded breaks in cellular DNA, in cancer cells. Any form of DNA-damaging agent know to those of skill in the art can be used DNA damage can typically be produced by radiation therapy and/or chemotherapy. DNA-damaging agents are also referred to as genotoxic agents. As used herein, "in conjunction with" shall mean that NKG2D-Fc is administered to a subject concurrently with one or more additional therapies (either simultaneously or separately but in close proximity), prior to, or after administration of one or more additional therapies.

Examples of radiation therapy include, without limitation, external radiation therapy and internal radiation therapy (also called brachytherapy) Energy sources for external radiation therapy include x-rays, gamma rays and particle beams, energy sources used in internal radiation include radioactive iodine (iodine$^{125}$ or iodine$^{131}$), and from strontium$^{89}$, or radioisotopes of phosphorous, palladium, cesium, indium, phosphate, or cobalt Methods of administering radiation therapy are well know to those of skill in the art.

Examples of DNA-damaging chemotherapeutic agents that may be particularly useful include, without limitation: Busulfan (Myleran), Carboplatin (Paraplatin), Carmustme (BCNU), Chlorambucil (Leukeran), Cisplatin (Platmol), Cyclophosphamide (Cytoxan, Neosar), Dacarbazme (DTIC-Dome), Ifosfamide (Ifex), Lomustme (CCNU), Mechlorethamme (nitrogen mustard, Mustargen), Melphalan (Alkeran), and Procarbazine (Matulane).

A number of other chemotherapeutic agents may be also used for the method described herein, either alone for in combination. These include: methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, cisplatin, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analog), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2' deoxycoformycin), Semustine (methyl-CCNU), Teniposide (VM-26), and Vindesine sulfate, but it is not so limited.

In addition, the following agents may be also useful for the instant invention: alkylating agents, such as carboplatin and cisplatm, mtrogen mustard alkylating agents, in nitrosourea alkylating agents, such as carmustme (BCNU), antimetabolites, such as methotrexate, folinic acid, purine analog antimetabolites, mercaptopurine, pyrimdme analog antimetabolites, such as fluorouracil (5-FU) and gemcitabme (Gemzar®), hormonal antineoplastics, such as goserelin, leuprohde, and tamoxifen, natural antineoplastics, such as aldesleukin, mterleukin-2, docetaxel, etoposide (VP-16), interferon alfa, paclitaxel (Taxol®), and tretinoin (ATRA), antibiotic natural antineoplastics, such as bleomycin, dact-momycm, daunorubicin, doxorubicin, daunomycm and mitomycins including mitomycin C, and vmca alkaloid natural antineoplastics, such as vinblastine, vincristine, vmdesme, hydroxyurea, aceglatone, adnamycin, Ifosfamide, enocitabme, epitiostanol, aclarubicm, ancitabme, nimustine, procarbazine hydrochloride, carboquone, carboplatm, car-mofur, chromomycm A3, antitumor polysaccharides, anti-tumor platelet factors, cyclophosphamide (Cytoxm®), Schizophyllan, cytarabme (cytosme arabmoside), dacarba-zine, thiomosine, thiotepa, tegafur, dolastatms, dolastatin analogs such as auπstatin, CPT-I 1 (mnotecan), mitozan-trone, vmorelbine, tenφoside, aminopteπn, carmmomycm, esperamicms (See, eg, U.S. Pat. No. 4,675,187, which is incorporated by reference herein), neocarzmostatin, OK 432, bleomycin, furtulon, broxundme, busulfan, honvan, peplomycm, bestatm (Ubemmexe), interferon-β, mepitios-tane, mitobromtol, melphalan, laninm peptides, lentman, Coπolus versicolor extract, tegafur/uracil, estramustme (es-trogen/mechlorethamme), thalidomide, and lenalidomide (Revhmide®).

Other suitable chemotherapeutics include proteasome inhibiting agents. Proteasome inhibitors block the action of proteasomes, cellular complexes that degrade proteins, particularly those short-lived proteins that are involved in cell maintenance, growth, division, and cell death. Examples of proteasome inhibitors include bortezomib (Velcade®), lac-tacystin (AG Scientific, Inc, San Diego, Calif.), MGI 32 (Biomol International, Plymouth Meeting, Pa.) PS-519, eponemycin, epoxomycm, aclacmomycm A, the dipeptide benzamide, CVT-63417, and vinyl sulfone tripeptide pro-teasome inhibitors.

In some embodiments, the methods described herein are used in conjunction with one or more other cancer treatments, including cancer immunotherapy. Cancer immuno-therapy is the use of the immune system to reject cancer. The main premise is stimulating the subject's immune system to attack the tumor cells that are responsible for the disease. This can be either through immunization of the subject, in which case the subject's own immune system is rendered to recognize tumor cells as targets to be destroyed, or through the administration of therapeutics, such as antibodies, as drugs, in which case the subject's immune system is recruited to destroy tumor cells by the therapeutic agents. Cancer immunotherapy includes an antibody-based therapy and cytokine-based therapy.

A number of therapeutic monoclonal antibodies have been approved by the FDA for use in humans, and more are underway. The FDA-approved monoclonal antibodies for cancer immunotherapy include antibodies against CD52, CD33, $CD_2O$, ErbB2, vascular endothelial growth factor and epidermal growth factor receptor. These and other antibodies targeting one or more cancer-associated antigen are thus suitable for use in a combination therapy to be administered in conjunction with NKG2D-Fc. Examples of monoclonal antibodies approved by the FDA for cancer therapy include, without limitation: Rituximab (available as Rituxan™), Trastuzumab (available as Herceptin™), Alemtuzumab (available as Campath-IH™), Cetuximab (available as Erbitux™), Bevacizumab (available as Avas-tin™), Panitumumab (available as Vectibix™), Gemtuzumab ozogamicin (available as Mylotarg™), Ibritu-momab tiuxetan (available as Zevalin™) and Tositumomab (available as Bexxar™). Examples of monoclonal antibodies currently undergoing human clinical testing for cancer therapy in the United States include, without limitation: WX-G250 (available as Rencarex™), Ipilimumab (available as MDX-010), Zanolimumab (available as HuMax-CD4), Ofatunumab (available as HuMax-CD20), ch14.18, Zalutu-mumab (available as HuMax-EGFr), Oregovomab (available as B43.13, OvalRex™), Edrecolomab (available as IGN-101, Panorex™), $^{131}$I-chTNT-IB (available as Cot-ara™), Pemtumomab (available as R-1549, Theragyn™), Lintuzumab (available as SGN-33), Labetuzumab (available as hMN14, CEAcide™), Catumaxomab (available as Removab™), CNTO 328 (available as cCLB8), 3F8, 177Lu-J591, Nimotuzumab, SGN-30, Ticilimumab (available as CP-675206), Daclizumab (available as Zenapax™), Epratuzumab (available as hLL2, LymphoCide™), $^{90}$Y-Epratuzumab, Galiximab (available as IDEC-114), MDX-060, CT-011, CS-1008, SGN-40, Mapatumumab (available as TRM-I), Apolizumab (available as HuID10, Remito-gen™) and Volociximab (available as M200).

Cancer immunotherapy also includes a cytokine-based therapy. The cytokine-based cancer therapy utilizes one or more cytokines that modulate a subject's immune response. Non-limiting examples of cytokines useful in cancer treatment include interferon-α (IFN-α), interleukin-2 (IL-2), Granulocyte-macrophage colony-stimulating factor (GM-CSF) and interleukin-12 (IL-12).

Furthermore, also contemplated is the gene-transfer of the NKG2D-Fc construct. For example, a retroviral vector encoding the NKG2D-Fc fusion sequence may be generated and used to transduce plasmacytoma cells. This strategy may reveal significant adjuvant function of the fusion in the context of irradiated, gene modified tumor cell vaccines. In this scheme, the secreted NKG2D-Fc protein may bind NKG2D ligands expressed on the tumor cell surface and then promote efficient Fc receptor mediated cross-presentation to dendritic cells recruited with GM-CSF.

EXAMPLES

Targeting the NKG2D Pathway for Cancer Immunotherapy

Previous analysis of the anti-MICA antibodies that naturally develop in MGUS patients, as well as those induced with irradiated, autologous GM-CSF secreting tumor cell vaccines and CTLA-4 blockade, indicated that anti-MICA monoclonal antibodies have therapeutic activity (Jinushi et al., 2006; Jinushi et al., 2008). Indeed, based in part upon these findings, Medarex, Inc. has initiated a program to generate fully human anti-MICA monoclonal antibodies for cancer treatment, which can be optimized for safe and effective clinical use. In conjunction with these developments, it is also desirable to develop and define the biologic and anti-tumor effects of targeting NKG2D ligands in murine models, such as myeloma cells, using transplantable plasmacytoma lines and the XBP-1 transgenic MGUS/MM model (Carrasco et al., 2007). Results obtained from such models are directly relevant and applicable for developing analogous therapeutics for human cancer patients.

As further described below, work presented herein demonstrate that the NKG2D-Fc fusion protein can: (1) trigger complement dependent lysis (complement-dependent cyto-toxicity or CDC); (2) trigger antibody dependent cellular cytotoxicity (ADCC); (3) promote the opsonization of myeloma cells for cross-presentation by dendritic cells; and, (4) antagonize the immunosuppressive effects of shed ligands.

In addition, further investigation was conducted to determine in transplantable plasmacytoma models whether the anti-tumor efficacy of the NKG2D-Fc fusion protein might be enhanced through combinations with systemic GM-CSF protein or vaccination with irradiated, GM-CSF secreting myeloma cells and CTLA-4 antibody blockade. The observed anti-tumor efficacy of the NKG2D-Fc fusion protein can also be readily confirmed in suitable animals models, such as the XBP-1 transgenic model, to evaluate the most promising therapeutic regimens by determining their impact on disease progression and immune function.

Furthermore, comparative studies were performed to examine NKG2D-Fc effects relative to those of anti-MICA antibodies. The results described below indicate that the NKG2D-Fc fusion protein may inhibit ligand-induced NKG2D activation on NK cells and CD8+ T cells, in contrast to anti-MICA antibodies, which do not interfere with receptor triggering by other ligands such as MICB or UL-16 binding proteins. The characterization of the NKG2D-Fc fusion protein provided in this disclosure should provide important new information for developing more effective cancer immunotherapy.

The following examples further illustrate the invention but are not intended to be limiting its scope in any way.

Example 1: Construction and Characterization of Murine NKG2D-Fc

The general strategy for the NKG2D-Fc construct is illustrated in FIG. 1 (shown as a dimer). For illustrative purposes, FIG. 1 depicts the NKG2D-Fc molecule (shown as a dimer) that contains two major portions: the extracellular domain of NKG2D and the activating Fc Ig domain. As indicated, the N-terminal portion of the molecule also contains the hinge region through which dimerization is mediated via disulfide bridge.

Since the sequences of murine NKG2D ligands differ significantly from their human counterparts (Lanier, 2005; Gonzalez et al., 2006), a novel fusion protein composed of the ligand-binding domain of murine NKG2D coupled to the Fc region of murine IgG2a (i.e., murine NKG2D-Fc) was constructed and was characterized for its biological activities. The data presented below indicate that the murine NKG2D-Fc detects both recombinant murine NKG2D ligands in an ELISA format and native NKG2D ligands present on the tumor cell surface, as assessed with flow cytometry. Moreover, the NKG2D-Fc fusion protein mediated potent and specific complement dependent lysis of NKG2D ligand expressing tumor cells. Consistent with these results, data from a series of studies as provided herein also show that the NKG2D-Fc chimera is capable of mediating the anti-tumor effector mechanisms. Similarly, the NKG2D-Fc chimera can destruct myeloma cells in vivo.

Figure 2:
FIG. 2 provides a schematic for a non-limiting example of the NKG2D-Fc construct. An N-terminal modified IL-2 signal sequence allows for optimal expression and secretion of NKG2D-Fc construct. Following the signal sequence is the mIgG2a Fc region, the IEGR (SEQ ID NO: 1) linker and the extracellular portion of the NKG2D molecule at the C-terminus.

A schematic of the murine NKG2D-Fc fusion protein is provided in FIG. 2. This construct contains the following components: (a) a N-terminal modified IL-2 signal sequence; (b) the $C_H2$ and $C_H3$ domains of murine IgG2a; (c) a four amino acid linker (IEGR; SEQ ID NO: 1); and, (d) the extracellular ligand-binding domain of murine NKG2D. An N-terminal modified IL-2 signal sequence allows for optimal expression and secretion of NKG2D/Fc construct. Detailed descriptions can be found, for example, in Zhang et al., 2004, J. Gene Med., 7: 354-65. Following the signal sequence is the mIgG2a Fc region. The $C_H2$ and $C_H3$ domains of murine IgG2a allows complement fixation and Fc receptor binding for opsonization an antibody-dependent cellular cytotoxicity. A linker, such as an IEGR (SEQ ID NO: 1) linker, functions as a spacer that in some cases provides flexibility. Finally, the extra-cellular portion of the NKG2D molecule at the C-terminus of the NKG2D-Fc construct was used, which corresponds to a ligand-binding portion of the molecule.

Figure 3:
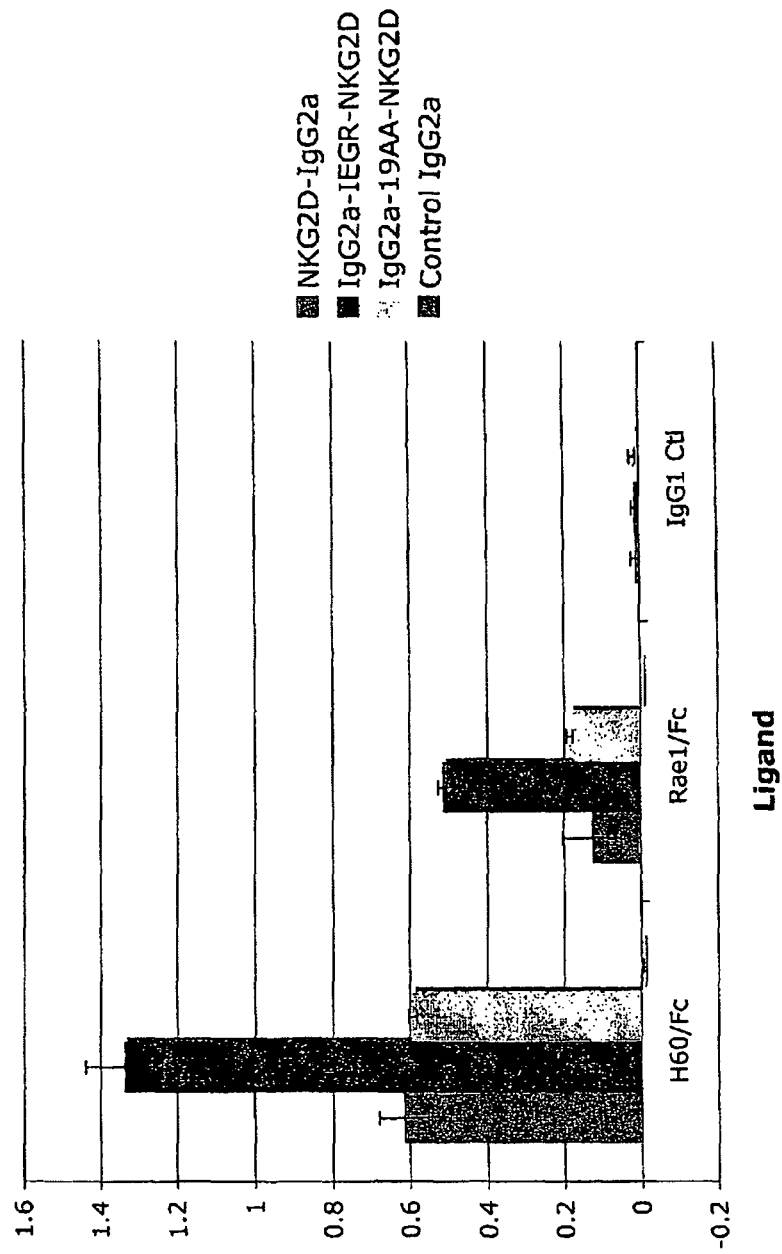
FIG. 3 provides a graph demonstrating the binding between three NKG2D-Fc constructs and NKG2D ligands as measured by ELISA. H60/Fc, Rae1e/Fc, or IgG1 control were used to coat plates and assess the ability of the various NKG2D constructs to bind the respective NKG2D ligands. The IgG2a-IEGR-NKG2D construct demonstrated greater binding to both H60 and Rae1e compared to either the NKG2D-IgG2a or the IgG2a-19AA-NKG2D constructs. None of the constructs bound to the control wells coated with human IgG1 (third column). The control mouse IgG2a did not show any binding to either H60/Fc or Rae1e/Fc.

As graphically shown in FIG. 3, the NKG2D-Fc fusion protein was characterized for its ligand binding activity. To test whether the NKG2D-Fc specifically detects murine NKG2D ligands, 50 ng of recombinant H60-Fc, Rae-1e-Fc (R&D Systems, Minneapolis, U.S.A.) or human IgG1 (Southern Biotechnology, Birmingham, U.S.A.) were coated overnight at 4° C. onto ELISA plates, which were then washed and blocked with a BSA/sucrose buffer. Subsequently, 250 ng of NKG2D-Fc fusion protein or isotype control were added for two hours, the plates were washed, a goat anti-mouse IgG2a-HRP secondary antibody was added for one hour, and the plate was then developed with a TMB liquid substrate. Results showed that the NKG2D-Fc fusion specifically bound recombinant H60-Fc and Rae-1e-Fc, but not human IgG1 in an ELISA, whereas a murine IgG2a isotype antibody did not.

Figure 4:
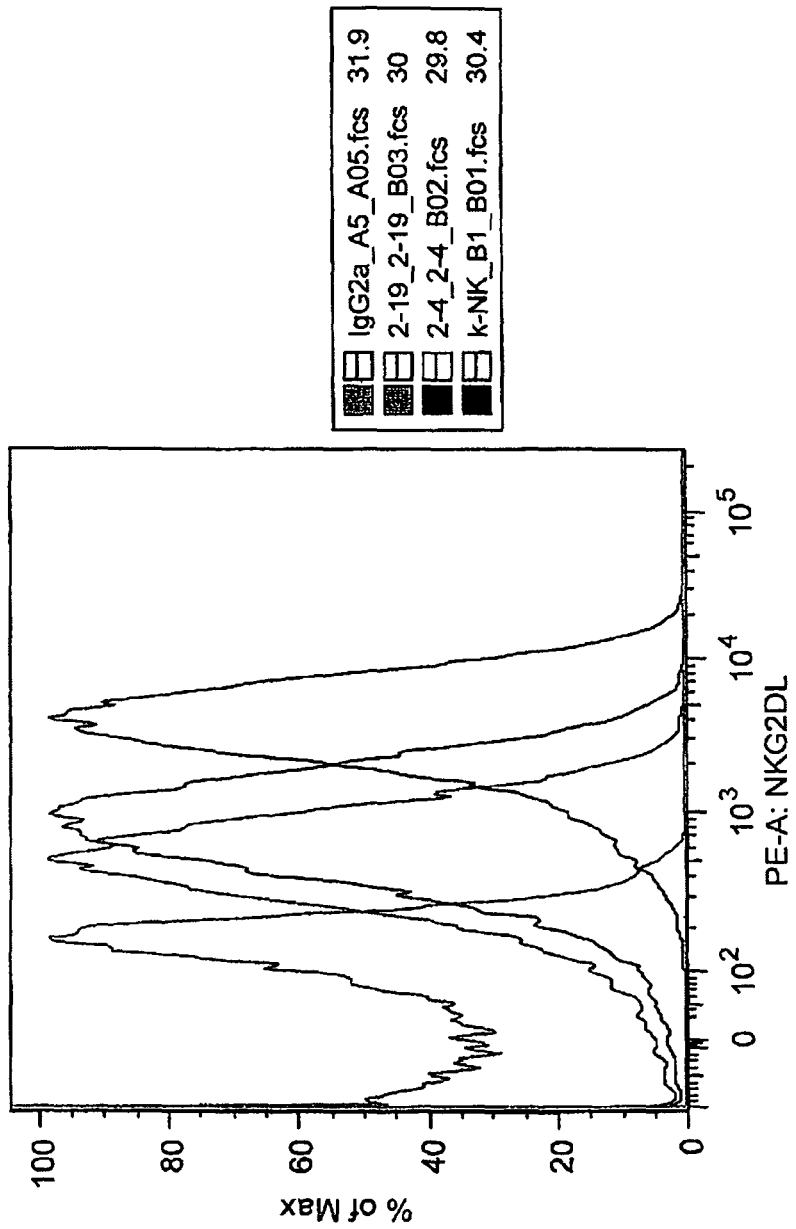
FIG. 4 provides a set of flow cytometry histograms. NKG2D-Fc constructs recognize NKG2D ligands expressed on YAC-1 cells. YAC-1 cells were stained with the respective NKG2D-Fc constructs, detected with a goat anti-mouse PE secondary antibody, and analyzed on a flow cytometer. While all three constructs demonstrated greater binding to the YAC-1 cells over the isotype control, the IgG2a-IEGR-NKG2D construct demonstrated the greatest binding compared to the moderate binding ability of the NKG2D-IgG2a construct and the weaker binding ability of the IgG2a-19AA-NKG2D construct.

Consistent with these results, the NKG2D-Fc fusion protein was also found to strongly stain YAC cells, an NK cell sensitive target, as determined by flow cytometry (FIG. 4).

Example 2: Anti-Myeloma Effects of an NKG2D-Fc Fusion Protein In Vitro

Cell Surface Expression of NKG2D Ligand

To determine the anti-myeloma effects of an NKG2D-Fc chimera in vitro, it was necessary to first establish that J558 and MPC11 plasmacytoma cells constitutively express murine NKG2D ligands. Flow cytometry was employed to determine cell surface expression of NKG2D ligands. To this end, $2.5 \times 10^5$ J558 or MPC11 cells were incubated with NKG2D-Fc fusion protein or IgG2a isotype as a negative control for 30 minutes. The samples were washed, then were incubated with a goat anti-mouse PE conjugated secondary antibody. The samples were then analyzed with a FACS Canto II flow cytometer. Flow cytometry results obtained showed that the NKG2D-Fc fusion protein stains J558 and MPC 11 plasmacytoma cells. These plasmacytomas thus tonically express NKG2D ligands and are thereby suitable for testing the immunologic and anti-tumor effects of the NKG2D-Fc fusion protein in syngeneic Balb/c mice.

Complement-Dependent Cytotoxicity (CDC)

To establish the specificity and biologic activity of the NKG2D-Fc chimera, the ability of the NKG2D-Fc fusion protein to stimulate ligand-specific complement dependent tumor lysis against the plasmacytoma lines was examined. Similar experiments have been conducted and reported for anti-MICA antibodies (see, for example, Jinushi et al., 2006).

Figure 5:
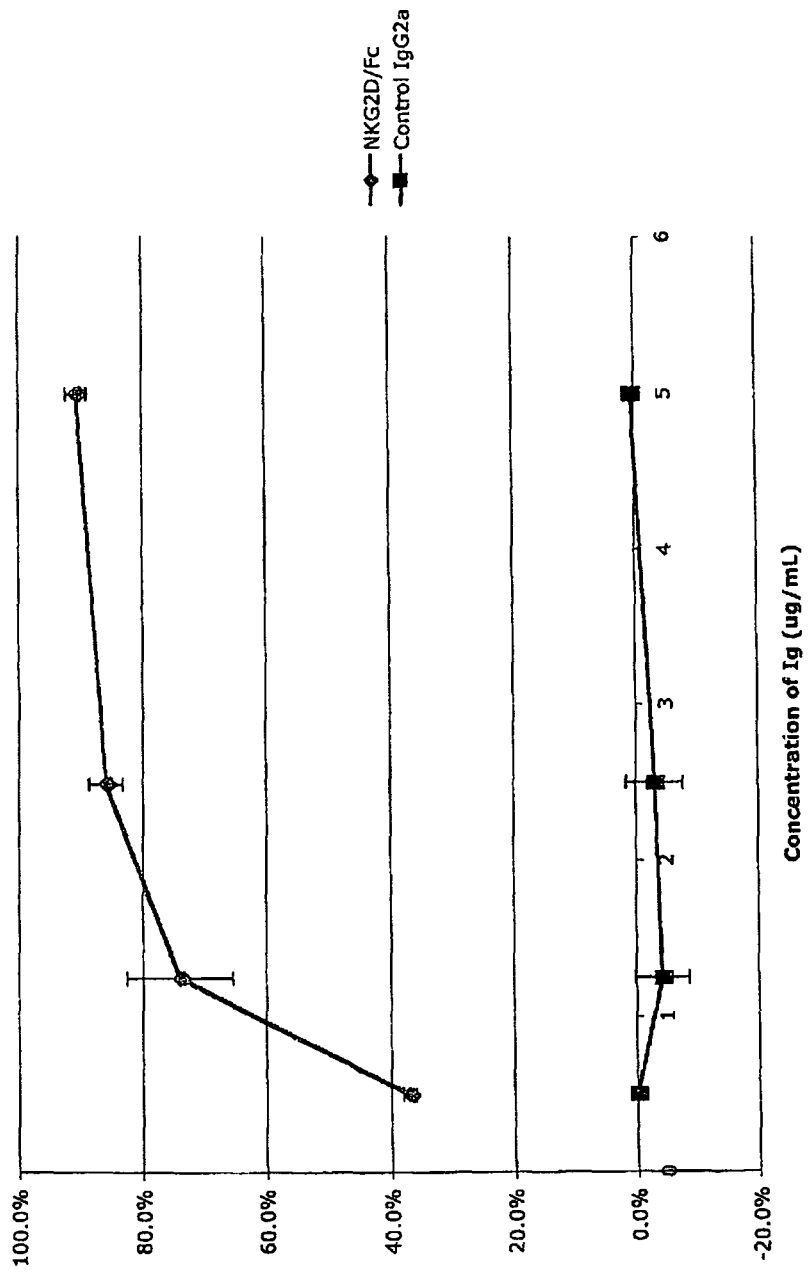
FIG. 5 provides a graph showing a dose-dependent effect of NKG2D-Fc on complement lysis in YAC-1 cells. YAC-1 cells were incubated with varying concentrations of either NKG2D-Fc (data points shown with ♦) or Control IgG2a (data points shown with ■) and rabbit complement (final concentration 1:20) for 2 hours at 37 degrees. The NKG2D-Fc, but not the control IgG2a, demonstrated increased lysis with increasing concentrations. Error bars indicate mean±standard deviation.

FIG. 5 demonstrates the ability of NKG2D-Fc to induce complement-dependent lysis of YAC-1 cells. The data show that at an approximately 2 µg/mL concentration, the NKG2D-Fc chimera was able to lyse ~80% of YAC-1 cells, whereas the control IgG2a had no significant effect.

Figure 6:
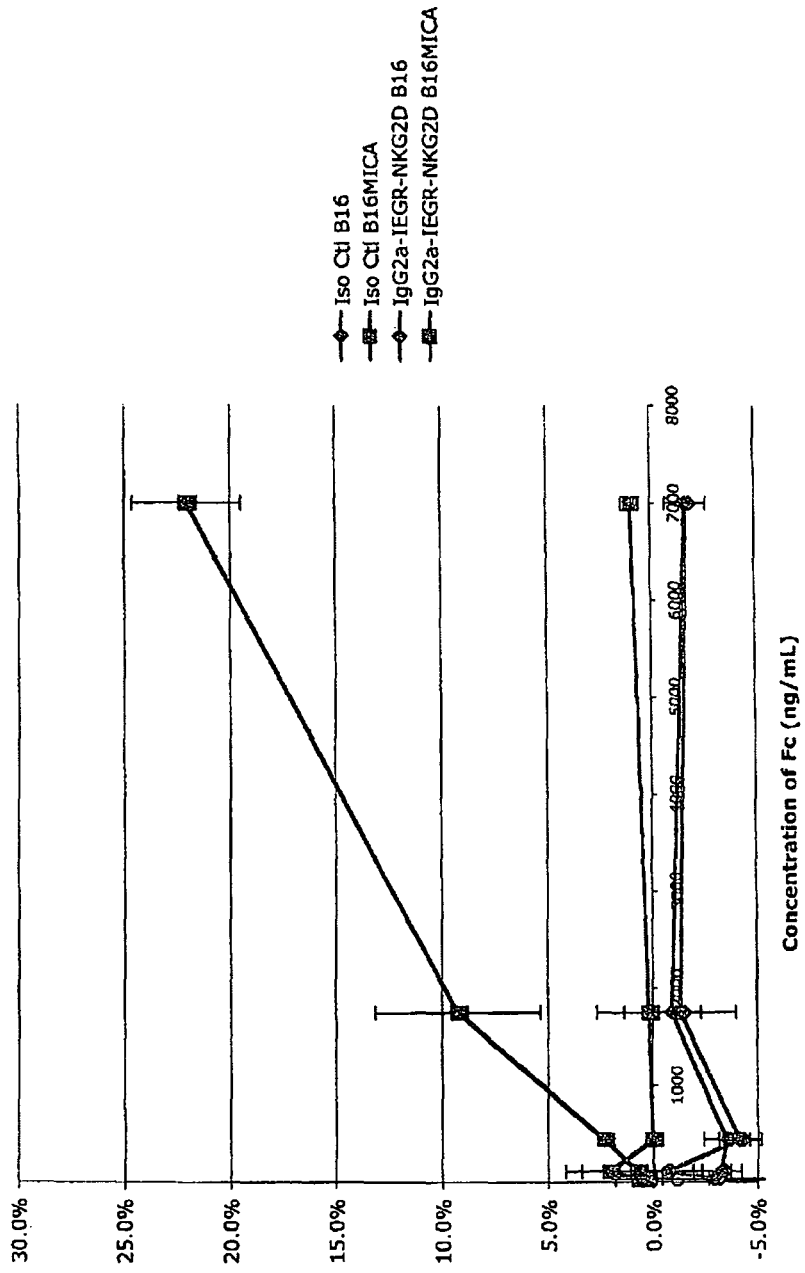
FIG. 6 provides a graph demonstrating a dose-dependent effect of NKG2D-Fc on cell lysis of B16 cells expressing MICA (B16/MICA). Wild type B16 cells were retrovirally transduced with the human NKG2D ligand MHC-I chain related protein A (MICA) as previously described. B16 and B16/MICA cells were incubated with rabbit complement (1:20) and either NKG2D-Fc or control IgG2a. NKG2D-Fc lysed B16/MICA cells, but not B16 cells in a dose dependent fashion. The control IgG2a showed no significant lysis of either B16 or B16/MICA cells. Error bars indicate mean±standard deviation.

Next, specific complement-dependent cell lysis was examined in wild type B16 cells, which do not express murine NKG2D ligands, and B16 cells engineered to express the NKG2D ligand, MICA (B16-MICA) (shown in FIG. 6). For the latter, B16 cells were subjected to retroviral-mediated gene transfer of MICA, which binds murine NKG2D.

B16-MICA and B16 cells were suspended at a density of $4 \times 10^6$ cells/ml in 0.3% BSA/RPMI media, the indicated amounts of NKG2D-Fc fusion or isotype control proteins were added together with rabbit complement (Cedarlane Labs, Burlington, U.S.A.) and 7-AAD (BD Biosciences, San Jose, U.S.A.) at 37° C. for two hours, and the cells were then analyzed with a FACS Canto II flow cytometer.

The NKG2D-Fc fusion protein mediated specific killing of B16-MICA cells, but not parental B16 cells, whereas a murine IgG2a isotype control failed to effectuate lysis of either line.

Antibody-Dependent Cellular Cytotoxicity (ADCC)

The capacity of the NKG2D-Fc fusion protein to stimulate ADCC was also explored. Activated peritoneal macrophages were harvested four days after thioglycollate instillation and then co-cultured for four hours with $^{51}$Cr labeled plasmacytoma cells in varying concentrations of the NKG2D-Fc fusion protein or isotype control (1-10 mg/ml based on our the studies of complement dependent lysis). Cells were stained with 7AAD then fated on CFSE+ targets.

Figure 8:
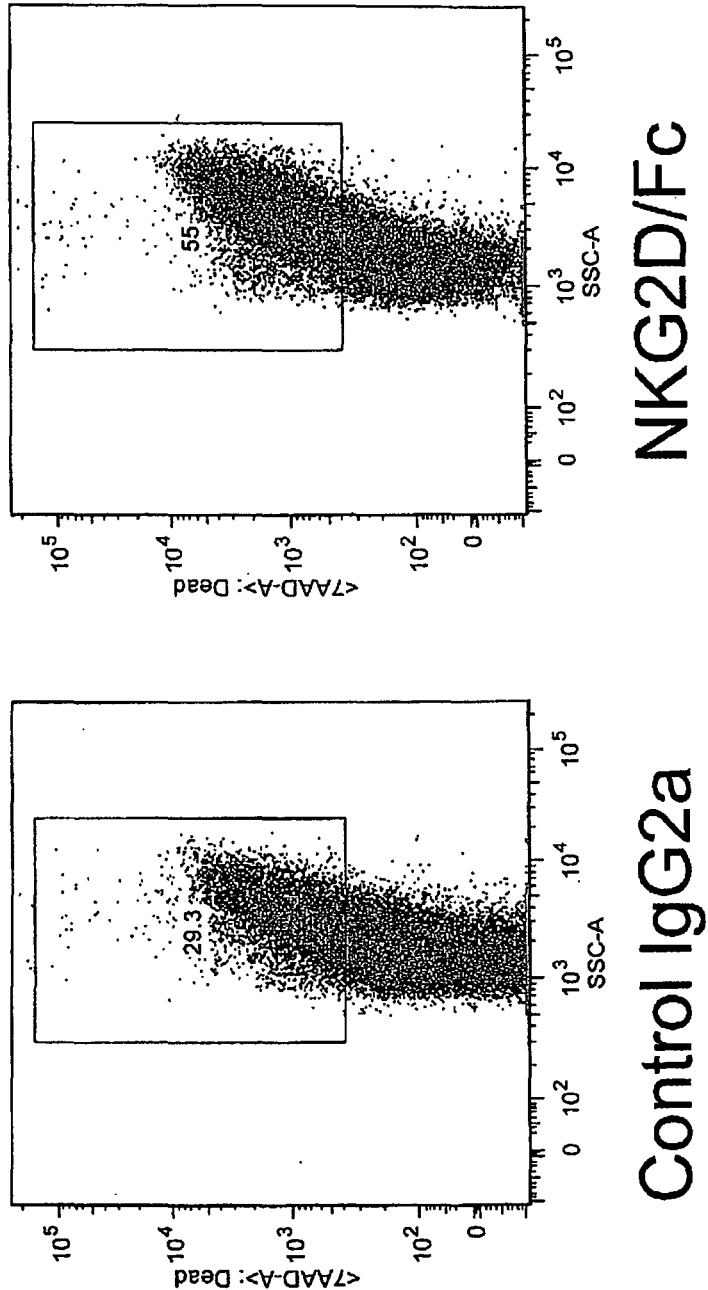
FIG. 8 provides two panels of flow cytometry data, demonstrating NKG2D-Fc-mediated ADCC in macrophages. NKG2D-Fc induced antibody dependent cellular cytotoxicity. Thioglycollated elicited macrophages were incubated overnight in a 24-well plate with 400,000 CFSE-labeled YAC-1 cells in the presence of either NKG2D-Fc (right panel) or Control IgG2a (final concentrations of 10 μg/mL; left panel). Cells were then harvested, stained with 7AAD, and analyzed on a flow cytometer. Cells are gated on CFSE+ cells, with the box reflecting 7AAD+ cells.

Data are shown in FIG. 8. Percent specific lysis was calculated using the formula: experimental release-spontaneous release/maximal release-spontaneous release. As shown, NKG2D-Fc induced ADCC in ~55% of the target cells, as compared to ~29% in negative control. Maximum release was obtained by incubating targets cells with 1% Triton-X.

Opsonization

Figure 9:
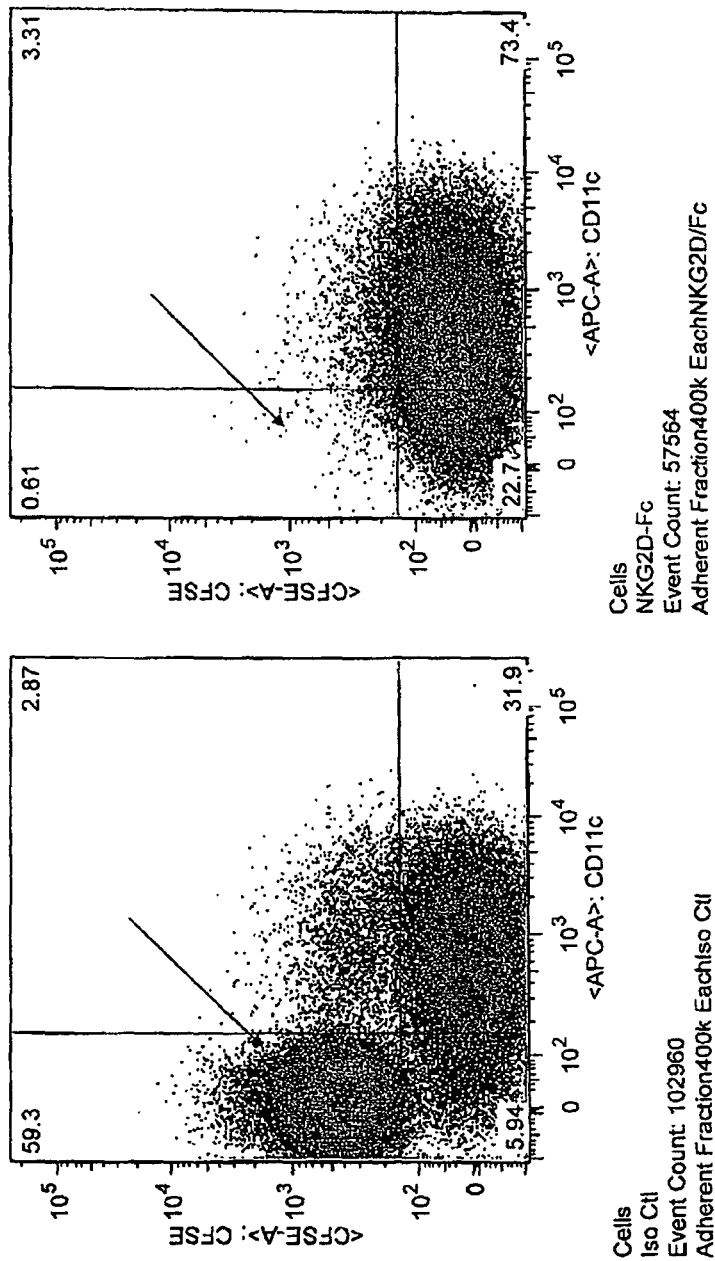
FIG. 9 provides two panels of flow cytometry data, demonstrating that NKG2D-Fc facilitates opsonization of YAC-1 cells by bone-marrow derived dendritic cells. Dendritic cells were incubated 1:1 with CFSE-labeled YAC-1 cells overnight with 10 μg/mL of either Control IgG2a (left panel) or NKG2D-Fc (right panel). Cells were then collected, stained with CD11c-APC, and analyzed on a flow cytometer. The arrow indicates the target YAC-1 population, which is present in the Control IgG2a wells, and absent in the NKG2D-Fc wells.

Next, opsonization assays were performed (FIG. 9), using methods similar to those earlier employed for the analysis of anti-MICA antibodies (Jinushi et al., 2006; Jinushi et al., 2008). Briefly, bone marrow-derived dendritic cells were generated in culture with RPMI 1640, 10% heat inactivated fetal calf serum, L-glutamine, penicillin/streptomycin, and GM-CSF/IL-4. Irradiated plasmacytoma cells were coated with the NKG2D-Fc fusion protein or isotype control and loaded onto the dendritic cells, which were then be matured with LPS.

Similar assays may be performed to test for T cell stimulation. CD3+ T cells (purified with magnetic beads from spleens) are co-cultured with the tumor cell loaded dendritic cells for 5-7 days, and then CD4+ and CD8+ T cells are purified with magnetic beads. CD4+ T cells are tested against plasmacytoma loaded dendritic cells for proliferative responses, as quantified by $^3$H-thymidine incorporation, and secretion of IFN-γ, IL-13, and IL-17 (representing prototypical members of Th1/Th2/Th17 subsets), as measured with ELISAs (Jinushi et al., 2007). Purified CD8+ T cells are evaluated for myeloma specific cytotoxicity using $^{51}$Cr release assays and IFN-γ production by ELISPOT (Jinushi et al., 2007). Multiple Balb/c derived plasmacytoma lines are used as targets to determine whether T cell reactivity is induced against shared or unique myeloma determinants, whereas YAC cells are employed as specificity controls. Additional T cell antigens to be considered in these murine plasmacytoma systems include XBP-1 and survivin.

Interaction with Soluble Ligand

To examine whether the NKG2D-Fc fusion protein can detect shed murine NKG2D ligands, a sandwich ELISA similar to that employed for measuring sMICA in clinical samples can be carried out. ELISA plates are first coated with the NKG2D-Fc reagent (or isotype control), then recombinant H60, Rae 1, or MULT-1 proteins (commercially available) are added, followed by anti-H60, anti-pan-Rae-1, and anti-MULT-1 antibodies (commercially available) as the detection reagents. Subsequently, supernatants from the panel of plasmacytoma cell lines can be tested for the production of shed ligands. Positive supernatants are evaluated for their ability to induce down-regulation of NKG2D surface expression in NK cells purified from the spleen (with DX5 beads), using procedures comparable to those employed for patient samples. The impact of soluble NKG2D ligands on NK cell lytic activity and IFN-γ production towards YAC targets are determined using $^{51}$Cr release assays and ELISAs. Lastly, based on an observation that soluble ligands diminish NKG2D levels, the NKG2D-Fc fusion protein can be evaluated for its ability to block these suppressive effects, analogous to the impact of anti-MICA antibodies in clinical specimens.

Example 3: Anti-Cancer Effects of an NKG2D-Fc Fusion Protein

Figure 7:
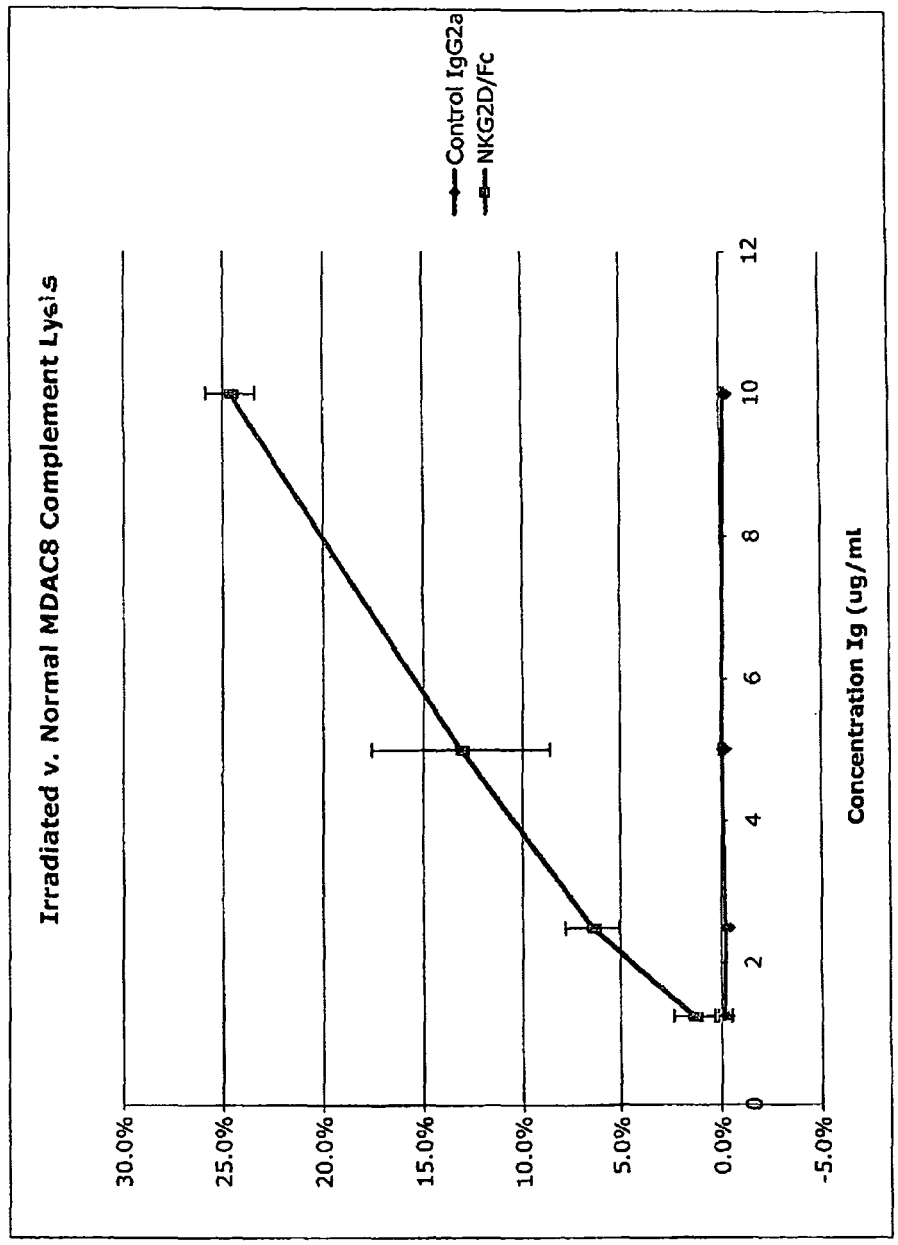
FIG. 7 is a graph illustrating a dose-dependent effect of NKG2D-Fc on complement lysis of MDAC8 cells. The cells were derived from a primary lung tumor in GM-CSF –/–, IFN-gamma –/–, and IL3–/– triple knockout mice, were incubated with rabbit complement (1:20) and either NKG2D-Fc or Control IgG2a. NKG2D-Fc (data points shown with ♦), but not control IgG2a (data points shown with ■) lysed target MDAC8 cells in a dose dependent fashion. Error bars indicate mean standard deviation.

The in vitro studies described above provide the range of anti-cancer effector mechanisms mediated by the NKG2D-Fc fusion protein. FIG. 7 provides results from in vitro complement lysis in a murine lung tumor model. In this set of experiments, MDAC8 cells were employed. MDAC8 cells were derived from a primary lung tumor in triple knockout mice that are lacking GM-CSF, IFN-γ and IL-3 (GM-CSF –/–, IFN-γ –/– & IL-3 –/–). The MDAC8 cells were incubated with rabbit complement (1:20 dilution) and either NKG2D-Fc as described in the previous section of the Example, or control IgG2a. As shown in FIG. 7, the NKG2D-Fc chimera caused lysis of the target MDAC8 cells in a dose-dependent fashion, while IgD2a had no effect. The result provides in vivo evidence that NKG2D-Fc can effectively induce complement-dependent cytotoxicity in the cancer model.

Additionally, the biologic effects of an NKG2D-Fc chimera may be examined in vivo using standard methods available to those skilled in the art. For example, varying numbers of plamacytoma cells may be injected subcutaneously into syngeneic adult Balb/c mice, followed by systematic administration of varying doses of the NKG2D-Fc fusion proteins or IgG2a isotype controls. Initially, an optimal fusion protein dose and schedule for inhibiting myeloma growth in the skin may be determined in a mouse model, starting typically with ~5 animals. In these studies, tumor growth may be monitored at 2-3 day intervals, the product of tumor diameters determined, and mice sacrificed when tumors reach 2 cm in greatest diameter or ulcerate. Once an active regimen has been established, experimental groups will be increased, for example to 10-20, so as to achieve statistical significance.

In addition to basic measurements of tumor size, whole body autopsies may be performed to examine potential inflammatory pathologies or other toxicities of NKG2D-Fc administration. Cellular infiltrates at plasmacytoma injection sites may be scored with antibodies to, for example, Gr-1, Mac-1, CD11c, DX5, CD3, CD4, CD8, FoxP3, and B220 to define the recruitment of innate and adaptive immune cells (Soiffer et al., 1998; Mach et al., 2000; Hodi et al., 2008). To corroborate these findings, tumor infiltrates may be obtained from plasmacytoma challenge sites using a Nocoprep (Axis-Shield) cell gradient separation, and the cells characterized by flow cytometry using this same profile of monoclonal antibodies.

Based on the notion that the NKG2D-Fc fusion protein may stimulate anti-myeloma T cell responses, CD8+ T cells from TILs and spleens may be purified and evaluated. The evaluation may include a number of parameters, such as activation by CD69 expression, cytotoxicity in $^{51}$Cr release assays, and IFN-γ production by ELISPOT. A panel of plasmacytoma cells and YACs may be used for targets, as described above. Purified CD4$^+$ T cells may also be stimulated with plasmacytoma loaded antigen-presenting cells, and then proliferative responses (e.g., $^3$H-thymidine incorporation) and cytokine production (e.g., IFN-γ, IL-13, IL-17 by ELISA) may be determined, as described above. The contributions of these T cell subsets to the anti-tumor effects of the NKG2D-Fc fusion protein may be delineated through the administration of monoclonal antibodies that deplete CD4$^+$ (clone GK1.5) or CD8$^+$ (clone 53.6.72) lymphocytes, as was reported previously (Dranoff et al., 1993).

After establishing the biologic activities of the NKG2D-Fc fusion protein in these studies, it may be determined whether co-administering GM-CSF protein systemically enhances tumor rejection. GM-CSF is a potent activator of ADCC and dendritic cell function and has been shown to augment the clinical efficacy of therapeutic monoclonal antibodies (Cartron et al., 2008; Waller, 2007). Thus, this cytokine may increase the potency of the NKG2D-Fc fusion protein. In this context, it was previously shown that systemic GM-CSF protein could be used to reconstitute a defect in contact hypersensitivity reactions evident in GM-CSF deficient mice (Gillessen et al., 2001). Based on these prior studies, a range of therapeutic regimens, such as cytokine dosages and schedules administered together with the NKG2D-Fc fusion protein, may be explored. Accordingly, favorable conditions are determined, where increased tumor cell destruction is observed as compared to the fusion protein alone. Where increased anti-tumor efficacy is observed, a detailed immune analysis of the combination therapy may be performed, using the approaches described above. In the event that GM-CSF (or other appropriate candidate cytokines) should fail to enhance tumor destruction. In this event, it is suggested that the tumor challenge sites are examined to see if there are any alterations in the numbers or mixtures of cells present. Potential changes would be examined in more detail; for example, increases in CD4$^+$ T cell numbers would prompt an evaluation of their proliferative capacity and cytokine profiles. These studies should reveal which anti-tumor effector mechanisms of the NKG2D-Fc fusion protein are most susceptible to modulation with systemic cytokine administration, e.g., GM-CSF.

A second combinatorial approach involves evaluating whether irradiated, GM-CSF secreting myeloma cell vaccines and/or CTLA-4 antibody blockade may enhance the activity of the NKG2D-Fc fusion protein (Dranoff et al., 1993; van Elsas et al., 1999; Hodi et al., 2008). Indeed, it was initially identified that anti-MICA antibodies in patients responded to these therapies (Jinushi et al., 2006). Retroviral mediated gene transfer may be used to engineer high-level GM-CSF secretion in the plasmacytoma cells. Anti-CTLA-4 antibodies can then be purified from supernatants of the 9H10 hybridoma using a HiTrap™ protein A sepharose column (Amersham Bioscience), as earlier reported (Enzler et al., 2007). Subsequently, conditions may be established, in which combinations of GM-CSF secreting plamacytoma vaccines and CTLA-4 blockade mediate anti-tumor activity against pre-existing plasmacytomas. A typical administration regime may involve three daily injections of 100 µg of anti-CTLA-4 mAbs with vaccination (1×10$^6$ irradiated cells), whereas initial tumor challenges may consist of 5×10$^5$ cells. Vaccination is initiated on day zero, and depending on the efficiency of tumor rejection, progressively delay the onset of therapy to define conditions in which the combination treatment shows only modest activity. It is then determined whether the addition of the NKG2D-Fc fusion protein to the GM-CSF secreting vaccine/CTLA-4 blockade combination under these conditions enhances myeloma cell destruction. Detailed immune analysis can be undertaken as described above if therapeutic potency is increased (comparisons with the GM-CSF secreting vaccine/CTLA-4 combination alone would also be made). In the absence of enhanced protection, tumor infiltrates may be initially characterized and then additional analysis are performed, depending on which cell types are most impacted, as discussed above.

Example 4: Anti-Myeloma Effects of the NKG2D-Fc Fusion Protein in XBP-1 Transgenic Mice As described herein, transplantable plasmacytoma lines provide many experimental advantages for exploring the biologic effects of the NKG2D-Fc fusion protein. In addition, the XBP-1 transgenic model may provide additional benefits to faithfully recapitulate the in pathogenesis of MGUS and MM (Carrasco et al., 2007). Thus, applying the insights gained from the previous studies, the impact of the NKG2D-Fc fusion protein on transgene-driven plasma cell transformation may be investigated. As a first step, the expression of NKG2D ligands on plasma cells longitudinally may be characterized and any correlation between their induction and the DNA damage response may be determined (Gasser et al., 2005). Bone marrow cells can be obtained from mice at varying ages and analyzed by flow cytometry will with a monoclonal antibody to CD138 and the NKG2D-Fc fusion protein. Results may be confirmed by showing that plasma cells from wild type littermates fail to show NKG2D-Fc binding, in contrast to plasma cells from transgenic mice harboring pathology (as determined by paraprotein levels). Consistent with this idea, recent studies have documented the upregulation of NKG2D ligands in transgenic models of B cell lymphomas (Unni et al., 2008; Guerra et al., 2008). Bone marrow samples that stain with the NKG2D-Fc fusion protein may be further tested for expression of specific NKG2D ligands using commercially available antibodies to pan-Rae-1 isoforms and MULT-1, etc. To evaluate activation of the DNA damage response, CD138$^+$ cells may be sorted, cell lysates are prepared, from which immunoblotting experiments may be performed with appropriate antibodies, such as antibodies against phosphorylated ATM and CHK-2 (commercially available).

Based on binding studies that demonstrate that the NKG2D-Fc fusion protein binds soluble NKG2D ligands in an ELISA, sera collected longitudinally from XBP-1 transgenic mice may be evaluated for the presence of shed ligands. Subsequently, correlation between the production of one or more of the identified NKG2D ligands and upregulation of ERp5 expression in transgenic plasma cells may be established. This may be determined by employing flow cytometry using the commercially available anti-human ERp5 sera, which cross-reacts with the murine protein.

The potential immunosuppressive effects of shed murine NKG2D ligands may initially be evaluated using techniques similar to those used for sMICA in clinical samples. Briefly, normal NK cells are isolated from the spleens of wild type mice and incubated for ~24 hours with control or soluble ligand containing sera; NKG2D expression and NK cell lytic activity/IFN-γ production in response to YAC cells are then determined. The ability of the NKG2D-Fc fusion protein to block the potential suppressive effects of soluble ligand may also be examined with this assay. To complement this analysis of sera, additional experiments are contemplated, in which NKG2D expression on NK and CD8+ T cells from transgenic mice harboring shed ligands may be evaluated. In addition, NK cell lytic activity and IFN-γ production in response to YAC cells may be similarly be measured.

Once the expression and function of NKG2D are characterized in the XBP-1 transgenic model, longitudinal studies may be undertaken to determine the impact of the NKG2D-Fc fusion protein on disease development and host immunity. For example, the activity of the fusion protein alone or in combination with systemic GM-CSF or vaccines/CTLA-4 blockade will be determined. The exact strategy to be adapted may in part depend upon what proves to be more effective against the transplantable plasmacytoma lines. Typically, periodic administration of therapy over prolonged periods are likely to be most effective. However, a feasible and effective schedule may be devised according to a number of relevant parameters described elsewhere herein. Monoclonal paraprotein measurements in serum may be used to help define the onset of clonal plasma cell expansion. In some cases, it may be desirable to test for differences in time to MM formation using the Wilcoxon test for censored data. Typically, sample size calculation is based on the power to detect differences in MM incidence at a fixed point in time. The endpoint for comparison may be the proportion of animals with MM at, for instance, 6 months and then at 12 months.

Animals in the longitudinal study may be monitored every several days, e.g., every 2-3 days, and are sacrificed upon showing significant clinical signs of illness. All other mice in the cohorts may undergo whole body autopsy to determine the extent of MM at the endpoints of the study. Detailed immune assessment may be performed upon sacrifice, using the approaches described above. Of particular interest may be the levels of soluble ligand or ligands, NKG2D surface expression on NK cells and CD8+ T cells, NK cell functional activity against YAC cells, and anti-myeloma CD4+ and CD8+ T cell responses. For the T cell assays, CD138+ plasma cells are sorted from the bone marrows of XBP-1 transgenic mice harboring disease (not entered into the therapeutic study) and are loaded into dendritic cells to serve as targets.

The studies outlined above should provide important new information that may guide the future clinical optimization, which exploits the NKG2D pathway as a broad target for cancer immunotherapy in a wide variety of cancer types that present abnormal levels of NKG2D ligand expression. As described elsewhere in more detail, fully human anti-MICA monoclonal antibodies may become available for clinical use. In comparison, however, the methods described herein employing NKG2D-Fc provide added advantage of eliciting broader effects in cancer therapy by virtue of its ability to bind multiple types of ligands.

A potential challenge for NKG2D-Fc-based cancer immunotherapy with respect to clinical optimization, e.g., safety and efficacy, is the possibility that NKG2D-Fc may inhibit normal cellular function of NKG2D. For example, NKG2D-Fc may block ligand induced NKG2D activation, which may prevent NKG2D-dependent NK cell killing and CD8+ T cell co-stimulation. Suppression of these pathways may result in diminished anti-tumor activity of the fusion protein. Nonetheless, the NKG2D-Fc retains the ability to opsonize myeloma cells for dendritic cell mediated cross-presentation as well as ADCC and complement dependent lysis. Thus, the methods of NKG2D-based immunotherapy described herein provide a useful new tool for targeting cancer cells.

An additional challenge in studying T cell immunity to murine plasmacytomas is the relative lack of knowledge regarding relevant tumor rejection antigens. To address this issue, it is possible to explore whether T cell responses to XBP-1 or survivin may be induced in the cross-presentation assays as described above. It has been demonstrated that XBP-1 specific T cells can be detected in MGUS patients, and several reports have defined the immunogenicity of survivin in human and murine systems (Friedrichs et al., 2006; Siegel et al., 2003; Zeis et al., 2003). For these antigens, a limited number of peptide epitopes predicted to show high MHC class I binding may be synthesized, using standard computer-based algorithms. If peptide-specific responses can be detected, these may be incorporated into the analysis of the in vivo effects of NKG2D-Fc fusion proteins. In the event these antigens do not prove active, ovalbumin cDNA sequences may be introduced into the plasmacytoma lines and tested for ovalbumin-specific T cells in the cross-presentation assay. This approach with a nominal model antigen may permit at least a formal demonstration of MHC class I and II restricted responses in this system.

Although unlikely based on prior studies of murine B cell lymphomas, the XBP-1 model might not in some circumstances result in high level NKG2D ligand expression on transformed plasma cells. In this event, the administration of Bortezomib and other compounds described above may be tested for their ability to enhance NKG2D ligand expression in vivo. This may provide an interesting model of combination drug and NKG2D-Fc fusion treatment.

REFERENCES

Ashkenazi et al. (1997) Immunoadhesins as research tools and therapeutic agents. *Current Opinion in Immunology*, 9: 195-200.

Caine et al. (1996) Recombinant Human PhenylethanolamineN-Methyltransferase: Overproduction in *Escherichia coli*, Purification, and Characterization. *Protein Expr. Purif.*, 8: 159-66.

Capon et al. (1989) Designing CD4 immunoadhesins for AIDS therapy. *Nature*, 337: 525-531.

Carrasco, D. R. et al. (2007) The differentiation and stress response factor XBP-1 drives multiple myeloma pathogenesis. *Cancer Cell*, 11, 349-60.

Cartron G. et al. (2002) Therapeutic activity of humanized anti-CD20 monoclonal antibody and polymorphism in IgG Fc receptor FcgammaRIIIa gene. *Blood*, 99: 754-758.

Cartron, G. et al. (2008) Granulocyte-Macrophage Colony-Stimulating Factor Potentiates Rituximab in Patients With Relapsed Follicular Lymphoma: Results of a Phase II Study. *J Clin Oncol.* 26: 2725-2731.

Cerwenka A, Baron J L. and Lanier L L. (2001) Ectopic expression of retinoic acid early inducible-1 gene (RAE-1) permits natural killer cell-mediated rejection of a MHC class I-bearing tumor in vivo. *Proc. Natl. Acad. Sci. USA* 98: 11521-6.

Cerwenka A, Baron J L. and Lanier L L. (2001) Ligands for natural killer cell receptors: redundancy or specificity. *Immunol. Rev.* 181:158-69

Chamow et al. (1996) Immunoadhesins: principles and applications, *Trends Biotechnol.*, 14: 52-60.

Cosman D, Müllberg J, Sutherland C L, Chin W, Armitage R, Fanslow W, Kubin M, and Chalupny N J. (2001) ULBPs, Novel MHC Class I—Related Molecules, Bind to CMV Glycoprotein UL16 and Stimulate NK Cytotoxicity through the NKG2D Receptor. *Immunity* 14: 123-133.

Diefenbach A, Jensen E R, Jamieson A M, and Raulet D H. (2001) Rae1 and H60 ligands of the NKG2D receptor stimulate tumour immunity. *Nature,* 413: 165-71.

Diefenbach, A., Tomasello, E., Lucas, M., Jamieson, A. M., Hsia, J. K., Vivier, E., and Raulet, D. H. (2002) Selective associations with signaling proteins determine stimulatory versus costimulatory activity of NKG2D. *Nature Immunol.,* 3: 1142-1149.

Dougan M and Dranoff G. (2008) Inciting inflammation: The RAGE about tumor promotion. *J. Exp. Med.,* 205: 267-270.

Dranoff, G. et al. (1993) Vaccination with irradiated tumor cells engineered to secrete murine granulocyte-macrophage colony-stimulating factor stimulates potent, specific, and long-lasting anti-tumor immunity. *Proc Natl Acad Sci USA,* 90: 3539-43.

Enzler, T. et al. (2007) Functional deficiencies of granulocyte-macrophage colony stimulating factor and interleukin-3 contribute to insulitis and destruction of beta cells. *Blood,* 110: 954-61.

Fonseca C and Dranoff G. (2008) Capitalizing on the immunogenicity of dying tumor cells. *Clin. Cancer Res.,* 14: 1603-1608.

Friedrichs, B., Siegel, S., Andersen, M. H., Schmitz, N. & Zeis, M. (2006) Survivin-derived peptide epitopes and their role for induction of antitumor immunity in hematological malignancies. *Leuk Lymphoma,* 47: 978-85.

Garrity et al. (2005) The activating NKG2D receptor assembles in the membrane with two signaling dimers into a hexameric structure. *Proc Nat'l Acad Sci U.S.A.,* 102: 7641-6.

Gasser, S., Orsulic, S., Brown, E. J. & Raulet, D. H. (2005) The DNA damage pathway regulates innate immune system ligands of the NKG2D receptor. *Nature,* 436: 1186-90.

Gilfillan S., Ho, E. L., Cella, M., Yokoyama, W. M., and Colonna, M. (2002) NKG2D recruits two distinct adapters to trigger NK cell activation and costimulation. Nature *Immunol.,* 3: 1150-1155.

Gillessen, S., Mach, N., Small, C., Mihm, M. & Dranoff, G. (2001) Overlapping roles for granulocyte-macrophage colony-stimulating factor and interleukin-3 in eosinophil homeostasis and contact hypersensitivity. *Blood,* 97: 922-8.

Gonzalez, S., Groh, V. and Spies, T. (2006) Immunobiology of human NKG2D and its ligands. *Curr Top Microbiol Immunol.,* 298: 121-38.

Groh V, Rhinehart R, Randolph-Habecker J, Topp M S, Riddell S R, and Spies T. (2001) Costimulation of CD8 T cells by NKG2D via engagement by MIC induced on virus-infected cells. *Nature Immunol.,* 2: 255-260.

Guerra, N. et al. (2008) NKG2D-deficient mice are defective in tumor surveillance in models of spontaneous malignancy. *Immunity,* 28: 571-80.

Hodi F S, Butler M, Oble D A, Seiden M V, Haluska F G, Kruse A, MacRae S, Nelson M, Canning C, Lowy I, Korman A, Lautz D, Russell S, Jaklitsch, Ramaiya N, Chen T C, Neuberg D, Allison J P, Mihm M C and Dranoff G. (2008) Immunologic and clinical effects of antibody blockade of cytotoxic T lymphocyte-associated antigen 4 in previously vaccinated cancer patients. *Proc. Natl. Acad. Sci. U.S.A.,* 105: 3005-3010.

Jinushi M and Dranoff G. (2007) *Immunosurveillance: Innate and Adaptive Anti-tumor Immunity.* In Cancer Immunotherapy: Immune Suppression and Tumor Growth. Eds. G C Prendergrast and E M Jaffee. Elsevier, pp 29-41.

Jinushi M, Hodi F S and Dranoff G. (2008) Enhancing the clinical activity of granulocyte-macrophage colony stimulating factor secreting tumor cell vaccines. *Immunol. Rev.,* 222: 287-298.

Jinushi M, Vanneman M, Munshi N C, Tai Y-T, Prabhala R H, Ritz J, Neuberg D, Anderson K C, Carrasco D R and Dranoff G. (2008) MHC class I chain-related protein A antibodies and shedding are associated with the progression of multiple myeloma. *Proc. Natl. Acad. Sci. U.S.A.,* 105: 1285-1290.

Jinushi, M. et al. (2007) MFG-E8 mediated uptake of apoptotic cells by APCs links the pro- and anti-inflammatory activities of GM-CSF. J Clin Invest 117, 1902-1913.

Jinushi, M., Hodi, F. S, and Dranoff, G. (2006) Therapy-induced antibodies to MHC class I chain-related protein A antagonize immune suppression and stimulate antitumor cytotoxicity. *Proc Natl Acad Sci USA.,* 103: 9190-5.

Kobayashi N, Pea-Cruz V, Karisola P, Dorfman D M, Jinushi M, Chernova I, Umetsu S E, Nagumo H, Zhu B, Butte M J, Sharpe A H, Dranoff G, Kaplan G G, casasnovas J M, Umetsu DT, DeKruyff R H and Freeman G J. (2007) T cell immunoglobulin mucine protein (TIM)-4 binds phosphatidylserine and mediates uptake of apoptotic cells. Immunity 27:927-940.

Lanier, L. L. (2005) NK cell recognition. *Annu Rev Immunol.,* 23: 225-74.

Lengyel et al. (2007) Mutations designed to destabilize the receptor-bound conformation increase MICA-NKG2D association rate and affinity. *J Biol. Chem.,* 282: 30658-666.

Li, P., Morris, D. L., Willcox, B. E., Steinle, A., Spies, T. and Strong, R. K. (2001) Complex structure of the activating immunoreceptor NKG2D and its MHC class I-like ligand MICA. *Nature Immunol.,* 2: 443-451.

Lin W M, Baker A C, Beroukhim R, Winckler W, Feng W, Marmion J M, Laine E, Greulich H, Tseng H, Gates C, Hodi F S, Dranoff G, Sellers W R, Thomas R K, Meyerson M, Golub T R, Dummer R, Herlyn M, Getz G and Garraway L A. (2008) Modeling genomic diversity and tumor dependency in malignant melanoma. *Cancer Res.,* 68: 664-673.

Liu et al. (2008) Engineering therapeutic monoclonal antibodies. *Immunological Reviews,* 222: 9-27.

Mach, N. et al. (2000) Differences in dendritic cells stimulated in vivo by tumors engineered to secrete granulocyte-macrophage colony-stimulating factor or Flt3-ligand. *Cancer Res.,* 60: 3239-46.

Nimmerjahn and Ravetch (2007) Antibodies, Fc receptors and cancer. *Curr. Opin. Immunol.,* 19(2): 239-45.

Nimmerjahn F. and Ravetch J V. (2006) Fcgamma receptors: old friends and new family members. Immunity, 24:19-28.

Siegel, S., Wagner, A., Schmitz, N. and Zeis, M. (2003) Induction of antitumour immunity using survivin peptide-pulsed dendritic cells in a murine lymphoma model. *Br J Haematol.,* 122: 911-4.

Soiffer, R. et al. (1998) Vaccination with irradiated autologous melanoma cells engineered to secrete human granulocyte-macrophage colony-stimulating factor generates potent antitumor immunity in patients with metastatic melanoma. *Proc Natl Acad Sci USA,* 95: 13141-6.

Steinle, A., Li, P., Morris, D. L., Groh, V., Lanier, L. L., Strong, R. K. and Spies, T. (2001) Interactions of human NKG2D with its ligands MICA, MICB, and homologs of the mouse RAE-1 protein family. *Immunogenetics*, 53: 279-287.

Strong and McFarland (2004) NKG2D and Related Immunoreceptors. *Advances in Protein Chemistry*, 68: 281-213.

Unni, A. M., Bondar, T. and Medzhitov, R. (2008) Intrinsic sensor of oncogenic transformation induces a signal for innate immunosurveillance. *Proc Natl Acad Sci USA.,* 105: 1686-91.

van Elsas, A., Hurwitz, A. A. and Allison, J. P. (1999) Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. *J Exp Med.,* 190: 355-66.

Waller, E. K. (2007) The role of sargramostim (rhGM-CSF) as immunotherapy. *Oncologist*, 12: Suppl 2, 22-6.

Wiemann, K. et al. (2005) Systemic NKG2D down-regulation impairs NK and CD8 T cell responses in vivo. *J Immunol.,* 175: 720-9.

Wu J, Song Y, Bakker A B, Bauer S, Spies T, Lanier L L and Phillips J H. (1999) An Activating Immunoreceptor Complex Formed by NKG2D and DAP10, *Science*, 285: 730-732.

Zeis, M. et al. (2003) Generation of cytotoxic responses in mice and human individuals against hematological malignancies using survivin-RNA-transfected dendritic cells. *J. Immunol.,* 170: 5391-7.

Zhang et al. (2004) Alteration in the IL-2 signal peptide affects secretion of proteins in vitro and in vivo. *J Gene Med.,* 7: 354-65.

NKG2D and its Ligands, First printed in R&D Systems' 2002 catalog, available at World Wide Web rndsystems. com/mini_review_detail_objectname_MR02_NKG2D. aspx.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for treating cancer comprising:
administering to a subject having an NKG2D ligand expressing cancer a composition containing a chimeric NKG2D-Fc polypeptide and a pharmaceutically acceptable carrier, in an amount effective to treat the cancer, wherein the chimeric NKG2D-Fc polypeptide binds an NKG2D ligand, wherein the chimeric NKG2D-Fc polypeptide comprises an NKG2D extracellular domain, and wherein the chimeric NKG2D-Fc polypeptide does not include a variable domain of an antibody, a $C_H1$ domain of an antibody, or a light chain of an antibody.

2. The method of claim 1, wherein the chimeric NKG2D-Fc polypeptide comprises a linking molecule which is not a contiguous portion of either NKG2D or Fc and which covalently joins an amino acid of NKG2D to an amino acid of Fc.

3. The method of claim 2, wherein the linking molecule is a peptide linker.

4. The method of claim 3, wherein the peptide linker is an IEGR (SEQ ID NO: 1) linker.

5. The method of claim 1, wherein the chimeric NKG2D-Fc polypeptide is a recombinant fusion protein.

6. The method of claim 5, wherein the NKG2D ligand expressing cancer is melanoma, lung cancer, plasma cell cancer, leukemia, lymphoma, ovarian cancer, colon cancer, pancreatic cancer or prostate cancer.

7. The method of claim 5, further comprising treating the subject with an additional cancer therapy that is not the chimeric NKG2D-Fc polypeptide, wherein the additional cancer therapy is an immunotherapy, a radiation therapy or a chemotherapy.

8. The method of claim 7, wherein the additional cancer therapy is a chemotherapy that damages DNA.

9. The method of claim 4, wherein the chimeric NKG2D-Fc polypeptide comprises an NKG2D extracellular domain.

10. The method of claim 4, wherein the chimeric NKG2D-Fc polypeptide is a recombinant fusion protein.

11. The method of claim 1, wherein the chimeric NKG2D-Fc polypeptide comprises an activating Fc domain.

12. The method of claim 11, wherein the activating Fc domain is an activating Fc domain of an IgG.

13. The method of claim 12, wherein the IgG is $IgG_1$.

14. The method of claim 1, wherein the chimeric NKG2D-Fc polypeptide further comprises a signal sequence.

* * * * *

UNITED STATES PATENT AND TRADEMARK OFFICE
CERTIFICATE OF CORRECTION

PATENT NO. : 10,865,233 B2
APPLICATION NO. : 13/140469
DATED : December 15, 2020
INVENTOR(S) : Dranoff et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 678 days.

Signed and Sealed this
Sixth Day of December, 2022

Katherine Kelly Vidal
*Director of the United States Patent and Trademark Office*